(12) United States Patent
Bai et al.

(10) Patent No.: US 10,378,025 B2
(45) Date of Patent: Aug. 13, 2019

(54) TOMATO YELLOW LEAF CURL VIRUS RESISTANCE

(75) Inventors: Yuling Bai, Wageningen (NL); Maarten Gertjan Verlaan, Utrecht (NL); Samuel Hutton, Tampa, FL (US)

(73) Assignees: WAGENINGEN UNIVERSITEIT, Wageninen (NL); UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 386 days.

(21) Appl. No.: 14/004,517

(22) PCT Filed: Mar. 12, 2012

(86) PCT No.: PCT/NL2012/050149
§ 371 (c)(1),
(2), (4) Date: Dec. 23, 2013

(87) PCT Pub. No.: WO2012/125025
PCT Pub. Date: Sep. 20, 2012

(65) Prior Publication Data
US 2014/0208459 A1    Jul. 24, 2014

(30) Foreign Application Priority Data
Mar. 11, 2011  (NL) ..................................... 2006378

(51) Int. Cl.
*A01H 5/10* (2018.01)
*C12N 15/82* (2006.01)
*A01H 5/08* (2018.01)
*C12Q 1/6895* (2018.01)

(52) U.S. Cl.
CPC ........... *C12N 15/8286* (2013.01); *A01H 5/08* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

2005/0278804 A1* 12/2005 Hoogstraten ............ A01H 1/04
800/280

FOREIGN PATENT DOCUMENTS

EP    1563727 A1    8/2005

OTHER PUBLICATIONS

Peters et al., 2009, The Plant Journal 58: 857-869.*
Batley and Edwards, 2007, In: Association Mapping in Plants, pp. 95-102.*
Ji et al., 2007, Molecular Breeding 20: 271-284.*
Solanum lycopersicum polynucleotide with GenBank accession No. AW092130, published May 18, 2001.*
de Castro et al., 2007, Eur. J. Plant Pathol. 117: 347-356.*
Weide et al., 1993, Genetics 135: 1175-1186.*
Foolad, 2007, International Journal of Plant Genomics, Article ID 64358, 52 pages, doi:10.1155/2007/64358.*
International Search Report dated Jun. 5, 2012, by the European Patent Office as the International Searching Authority in International Patent Application No. PCT/NL2012/050149.
Peters et al., Solanum lycopersicum cv. 1706 chromosome 6: distribution and abundance of genes and retrotransposable elements, The Plant Journal, Jun. 1, 2009, pp. 857-869, vol. 58, No. 5, Blackwell Publishing Ltd.
Ji et al. Ty-3, a begomovirus resistance locus near the Tomato yellow leaf curl virus resistance locus Ty-1 on chromosome 6, Molecular Breeding, Apr. 6, 2007, pp. 271-284, vol. 20, No. 3, Kluwer Academic Publishers, DO.
Perez De Castro et al., Identification of a CAPS marker tightly linked to the Tomato yellow leaf curl disease resistance gene Ty-1 in tomato, European Jr. of Plant Pathology, Feb. 22, 2007, pp. 347-356, vol. 117, No. 4, Kluwer Academic Publishers, DO.
Barbieri et al., Introgression of resistance to two Mediterranean virus species causing tomato yellow leaf curl into a valuable traditional tomato variety, Rivista di Pathologia Vegetale, Jan. 1, 2010, pp. 485-493, vol. 92, No. 2.
Zamir, D., et al., "Mapping and introgression of a tomato yellow leaf curl virus tolerance gene, Ty-1", Theoretical and Applied Genetics, 1994, vol. 88, pp. 141-146.

* cited by examiner

*Primary Examiner* — Bratislav Stankovic
(74) *Attorney, Agent, or Firm* — Dentons US LLP

(57) ABSTRACT

Molecular markers are described for determining the presence or absence of a gene conferring resistance to tomato yellow leaf curl virus from *S. chilense* (Ty-1) in a host plant. Also described, are methods for producing a host plant comprising a gene conferring resistance to tomato yellow leaf curl virus from *S. chilense* (Ty-1), including the analysis of the presence or absence of the molecular markers. A plant, and parts thereof, obtained by such a method are also described.

Figure 1:
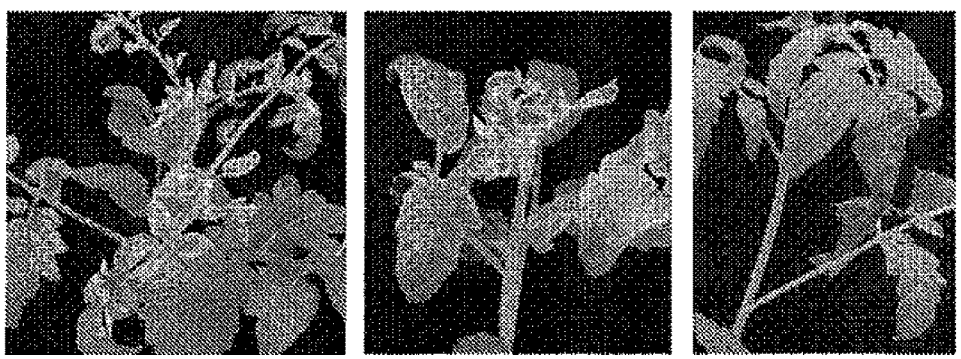

8 Claims, 10 Drawing Sheets
Specification includes a Sequence Listing.

Figure 7

```
>Ty-1
ATGGGTGATCCGTTGATTGAAGAAATTGATGTTCCTTCTTGTATAACTGGATGCACCTTTACCATATTCTGTAGAGACGATGCTTGATAGAA
TCTGCAAGGAGCAGGGGCAAAAACCACCGTGTACTGGCATTAGAAGGAGGCTGAGCTCTATTGGTGAAAAAGGGTCATTAGAAATGCTCAA
AATAATATCACGTCGTCCTATCAAGAAGAGTCTCTCTGCTTTTCTTGTTTACATGATTGATCGCTACCCGGATTGTCTCTCCTCTTCCTCT
AGCCCATTCAAT GTCTACTCAAACGCTCTTCTTCCCCT TCTATTTCCATCTCCAGAGGGTAAACGTTTACAAGGTGAAAGTTCTTCTA
AATCAAAGCTTGAGATGGGCTTATTGGCCTGTGCAAGCCCTCAGAAAGTTGCTCGCCAGTTATCATTTTGCGAGGAGCCTGAATCTAACTG
TAGAAGAACCTCCCCTTATGTCAGCCAACAGTTGATGATCCTCAATGAACTTGAATTTAGAAAATTGTTTTTGGTACTGAGCTACATTGGA
TGCAACAAGTTGGAAGATGTTATATCCCCTCAAATTGCTGATGATATTGTAAGAAAGAAA ATCTTTCCATGACTGATTTTGAATCAGAAA
TTTGGAATGCTTTTGGAAAAGCATGTTATGCTGTGTCAGATAGATCAAAGTACTTAGACTGGAATTGCAGAAAGACACATATCTACTATTG
CCACATTAAGCAGAACGGAT CTGT CCTTCAAGGGTCCATACTTGAACACA AAGGACTCACTTACAGAGAGCCCTGGGAGATGACAAT
GTACTGATTGTCAAATTTGTTGAAGATACAAGTTGTGCCAATATAATTCTCGAGGAAGGCATTCTTGTTGGCTTGAGACGTTACCGTTTCT
TTGTGTATAAAGATGATAAAGAGAGGAAGAAAAGTCCAGCTATGATGAAGACAAAAACTGCTTCTTTGAAGTGCTACTTTGTTAGGTTTGA
GTCCATTGGAACCTGC ATGATGGAGAATCCTATGTATTTTCTACCAAAACAATCAGTCAAGCAAGGTGTAAATTCATGCATGTGCATATG
GTTTCTAATATGGCAAAATATGCAGCCAGGCTTTCCTTAATTCTATCAAAGACTATTAAGCTTCAA GATCTTGATTCTGTCACCATTG
AAAGAATCGAAGATATACTTTGTCGGGATGAAAATGGTTGTATTATTCAAGATGAAGACGGCGAACCTCGTATACATACTGATGGTACTGG
TTTCATATCAGAAGATTTAGCTATGCATTGTCCCAAAGATTTTCAAAAGCAGAATATATAAAAGATGAAAATTATGAGAATTTTGTTGAT
ATCGTGGACCTTGATGACGTGAATGTAGAAAGAAGAG GAGTGTATCT G AATAGG AACCGCCTTTGTTGATGCAGTGCCGTTTGTTCT
TCAACGGTTGTGCTGTGAAGGGGACTTTTCTTGTCAATAGAAAGATTGGATCACGAAAAATTCATATTAGACCCTCAATGGTGAAGGTTGA
GATAGACCCAACAATTTCAAGTATACCAACTTTTGACTCATTGGAGATAGTTGCAATCAGTCATAGACCAAATAAGGCATATCTGTCCAAG
AATTTAATCTCTCTGCTGAGCTACGGAGGAGTCCATAAAGAATACTTT TGGAGCTTTTGGGAAGTGCACTGGAAGAGACGAAACAAGTAT
ATTTGAGGAACGGGCAGCTCTAAAAGTTGCTATCAACTATAGAGAAATGGATGATGAATGTCTAACAGCAAGGATGATATCGTCTGGGAT
ACCTCTCAATGAACCTCATCTCCATG TCGCTTGTCTAGGCTTGCAAAGATTGAAAGAACTAAGCTTAGAGGAGGAAAGCTTCCTATAAGT
GACAGTTTTTATCTTATGGGAACAGCTGACCCCACTGGTGTACTGGAAAGCAATGAAGTCTGTG TATTCTAGATAATGGCCAAGTATCTG
GGCGTGTTTTGGTCTACAGAAATCCTGGTCTTCACTTTGGAGATGTGCATGTGATGAAAGCGCGATATGTGGAAGAGCTTGCAGATGTTGT
TGGTGATGCCAAATATGGTATATTTTTTTCAACTAAAGGCCCGAGGTCAGCTGCTACTGAGATTGCAAATGGTGACTTTGATGGTGATATG
TATTGGGTTTCCATAAACCGTAAGTTGGTAGATTCTTATACAACAAGTAGACCATGGATTCGCATGCATTCAACTCCTAA GCAGTTAGCA
AAAAACCAAGTGAATTTTCAGCTGATGAATTGGAATATGAGCTTTTCAGGCAATTTCTGGAAGCAAAGTCTAAAGGTGCCAATATGTCTCT
GGCAGCTGATAGCTGGCTGGCATTTATGGATCGTCTTCTGA GCTGCCGAGATGATAATGTGGATGATATGCATAGCTTGAAAGGCAAGATG
CTTCACCTGATTGACATCTACTATGATGCATTAGATGCACCTAAAAAGCGGGAAGAAGGTTAGCATCCCTCATTATCTGAAGGCAAACAAGT
TCCCCCACTATATGGAAAAAGGGAACTCCTGCAGCTATCATTCAACTTCTATTCTGGGTCAGATTTATGATCATGTCGACTCATATCCAGA
TGAAGATTTGTGTATAACAGAGATCTCTAAACTGCCTTGCTTTGAAGTTGAAATCCCTCAAAGATGCATGACATTGTGGAGAGGAAGATAT
GAAGAGTACAAAAAGGATATGACAC GGCCATGAACTT GATTGTGAACTTAGAATCACCTCTTGCAATGAAGTTATAAAGAAGTACAAGA
TGTTGCTATATGGTGCTGTGGAGTTTGAACAAACAGTAAGAAAGACTGAAGACATTTTCGATGAAGCCCTTGCAATATATCATGTAACATA
TGATAATGCAAGGATCACATACAGCATAGAGAAATGTGGTTTTGCTTGGAAAGTAGCTGGTTCTGCGCTTTGCAGGATCCACGCCATGTAT
CGCAAGGAAAAAGACTTGCCCATTTTGCCATCGGTTTTGCAGGAAATACTC TGTATTGTAACATTGAAGTGATCAATAAATATCTACT
TAGTATTCT

>MoneyMaker
ATGGGTGATCCGTTGATTGAAGAAATTGATGTT------------
CTGGATGCACCTTTACCATATTCTGTAGAGACGATGCTTGATAGAATCTGCAAGGA
GCAGGGGCAAAAACCACCGTGTACTGGCATTAGAAGGAGGCTGAGCTCTATTGGTGAAAAAGGGTCATTAGAAATGCTCAAAATAATATCA
CGTCGTCCTATCAAGAAGAGTCTCTCTGCTTTTCTTGTTTACATGATTGATCGCTACCCGGATTGTCTCTCCTCTTCCTCTAGCCCCTTCA
AT GTCTACTCAAACGCTCTTCTTCCCCT TCTCTTTCCATCTCCAGAGGGTAAACGTTTACAAGGTGAAAGTTCTTCTAAATCAAAGCT
TGAGATGGGCTTATTGGCCTGTGCAAGCCCTCAGAAAGTTGCTCGCCAGTTATCATTTTGCGAGGAGCCTGAATCTAACTGTAGAAGAACC
TCCCCTTATGTCAGCCAACAGTTGATGATCCTCAATGAACTTGAATTTAGAAAATTGTTTCTGGTACTGAGCTACATTGGATGCAACAAGT
TGGAAGATGTTATATCCCCTCAAATTGCTGATGATATTGTAAGAAAGAAA ATCTTTCCATGACTGATTTTGAATCAGAAATTTGGAATGC
TTTTGGAAAAGCATGTTATGCTGTGTCAGATAGATCAAAGTACTTAGACTGGAATTGCAGAAAGACACATATCTACTATTGCCACATTAAG
CAGAACGGAT CTGT CCTTCAAGGGTCCATACTTGAACACA AAGGACTCACTTACAGAGAGCCCTGGGAGATGACAATGTACTGATTG
TAAAATTTGTTGAAGATACAAGTTGTGCCAATATAATTCTCGAGGAAGGCATTCTTGTTGGCTTGAGACGTTACCGTTTCTTTGTGTATAA
AGATGATAAAGAGAGGAAGAAAAGTCCAGCTATGATGAAGACAAAAACTGCTTCTTTGAAGTGCTACTTTGTTAGGTTTGAGTCCATTGGA
ACCTGC ATGATGGAGAATCCTATGTATTTTCTACCAAAACAATCAGTCAAGCAAGGTGTAAATTCATGCATGTGCATATGGTTTCTAATA
TGGCAAAATATGCAGCCAGGCTTTCCTTAATTCTATCAAAGACGATTAAGCTTCAA GATCTTGATTCTGTCACCATTGAAAGAATTGA
AGATATACTTTGTCGGGATGAAAATGGTTGTATTATTCAAGATGAAGACGGCGAACCTCGTATACATACTGATGGTACTGGTTTCATATCA
GAAGATTTAGCTATGCATTGTCCCAAAGATTTTTCAAAAGCAGAATATATAAAAGATGAAAATTATGAGAATTTTGTTGATATCGTGGACC
TTGATGACGTGAATGTAGAAAGAAGAG GAGTGTATCT G AATAGG AACCGCCTTTGTTGATGCAGTGCCGTTTGTTCTTCAATGGTTG
TGCTGTGAAGGGGACTTTTCTTGTCAATAGAAAGATTGGATCACGAAAAATTCATATTAGACCCTCAATGGTGAAGGTTGAGATAGACCCA
ACAATTTCAAGTATACCAACTTTTGACTCATTGGAGATAGTTGCAATCAGTCATAGACCAAATAAGGCATATCTGTCCAAGAATTTAATCT
CTCTGCTGAGCTACGGAGGAGTCCATAAAGAATACTTT TGGAACTTTTGGGAAGTGCCTGGAAGAGACGAAACAAGTATATTTGAGGAA
ACGTGCAGCTCTAAAAGTTGCTATCAACTATAGAGAAATGGATGATGAATGTCTAACAGCAAGGATGATATCGTCTGGGATACCTCTCAAT
GAACCTCATCTCCATG TCGCTTGTCTAGGCTTGCAAAGATTGAAAGAACTAAGCTTAGAGGAGGAAAGCTTCCTATAAGTGACAGTTTTT
ATCTTATGGGAACAGCTGACCCCACTGGTGTACTGGAAAGCAATGAAGTCTGTC TATTCTAGATAATGGCCAAGTATCTGGGCGTGTTTT
GGTCTATAGAAATCCTGGTCTTCACTTTGGAGATGTACATGTGATGAAAGCGCGATATGTGGAAGAGCTTGCAGATGTTGTTGGTGATGCC
AAATATGGTATATTTTTTCAACTAAAGGCCCGAGGTCAGCTGCTACTGAGATTGCAAATGGTGACTTTGATGGTGATATGTATTGGGTTT
CCATAAACCGTAAGTTGGTAGATTCTTATACAACAAGTAGACCATGCATTGCAATGCATTCAACTCCTAA GCAGTTAGCAAAAAACCAAG
TGAATTTTCAGCTGATGAATTGGAATATGAGCTTTTTAGGCAATTTCTGGAAGCAAAGTCTAAAGGTGCCAATATGTCTCTGGCAGCTGAT
AGCTGGCTGGCATTTATGGATCGTCTTCTGA GCTGCCGAGATGATAATGTGGATGATATGCATAGCTTGAAAGGCAAGATGCTTCACCTGA
TTGACATCTACTATGATGCATTAGATGCACCTAAAAAGCGGGAAGAAGGTTAGCATCCCTCATTATCTGAAGGCAAACAAGTTCCCCCACTA
TATGGAAAAAGGGAACTCCTGCAGCTATCATTCAACTTCTATTCTGGGTCAGATTTATGATCATGTCGACTTTGATGGTGATATGTATTTG
TGTATAACAGAAATCTCTAAACTGCCTTGCTTTGAAGTTGAAATCCCTCAAAGATGCATGACATTGTGCGACTATAAAGAAGTACAAGATTTG
TGTATAACAGAAATCTCTAAACTGCCTTGCTTTGAAGTTGAAATCCCTCAAAGATGCATGACATTGTGGAGAGGAAGATATGAAGAGTACA
AAAAGGATATGACAC GGCCATGAACTT GATTGTGAACTAAGAATCACCTCTTGCAATGAAGTTATAAAGAAGTACAAGATGTTGCTATA
TGGTGCTGTGGAGTTTGAACAAACAGTAAGAAAGACTGAAGACATTTTCGACGAGGCCCTTGCAATATATCATGTAACATATGATAATGCA
AGGATCACATACAGCATAGAGAAATGTGGTTTTGCTTGGAAAGTAGCTGGTTCTGCGCTTTGCAGGATCCACGCCATGTATCGCAAGGAAA
AAGACTTGCCCATTTTGCCATCGGTTTTGCAGGAAATACTC CGTATTGTAACATTGAAGTGATCAATAAATATCTACTTAGCATTCT
```

| Marker name | Position SL2.50ch06 (Mbp) |
|---|---|
| C2_At4g01900 | 3.33 |
| M304P16-2 | 3.57 |
| M242H19-2 | 16.39 |
| Mi23 | 23.22 |
| Aps-1 | 23.69 |
| M295L11-1 | 23.69 |
| C2_At5g61510 | 23.70 |
| M309K01-1 | 23.73 |
| M271L05-4 | 24.31 |
| JB-1 | 24.60 |
| M040F08-2 | 24.91 |
| Msc09983-6 | 25.04 |
| TG231 | 25.37 |
| REX-1 | 26.33 |
| TG97 | 29.59 |
| M067G18-1 | 32.66 |
| T1563 | 32.77 |
| Msc01216-6 | 33.07 |
| M026P18-1 | 33.31 |
| M302A23-3 | 33.54 |
| T0774 | 33.54 |
| M082G10-5 | 33.71 |
| MSc05732-3 | 34.03 |
| MSc05732-4 | 34.11 |
| Ty3-M3 | 34.33 |
| Ty3-M5 | 34.40 |
| Ty3-M6 | 34.47 |
| cLEG-31-P16 | 34.50 |
| MSc05732-14 | 34.71 |
| MSc05732-18 | 35.09 |
| PG9 | 35.19 |
| C2_At3g11210 | 35.27 |
| M005H10 | 35.28 |
| M304P16-2 | 35.72 |
| TG25 | 37.32 |

Figure 9. Positions of various markers on SL2.5ch06.

Genetic map positions
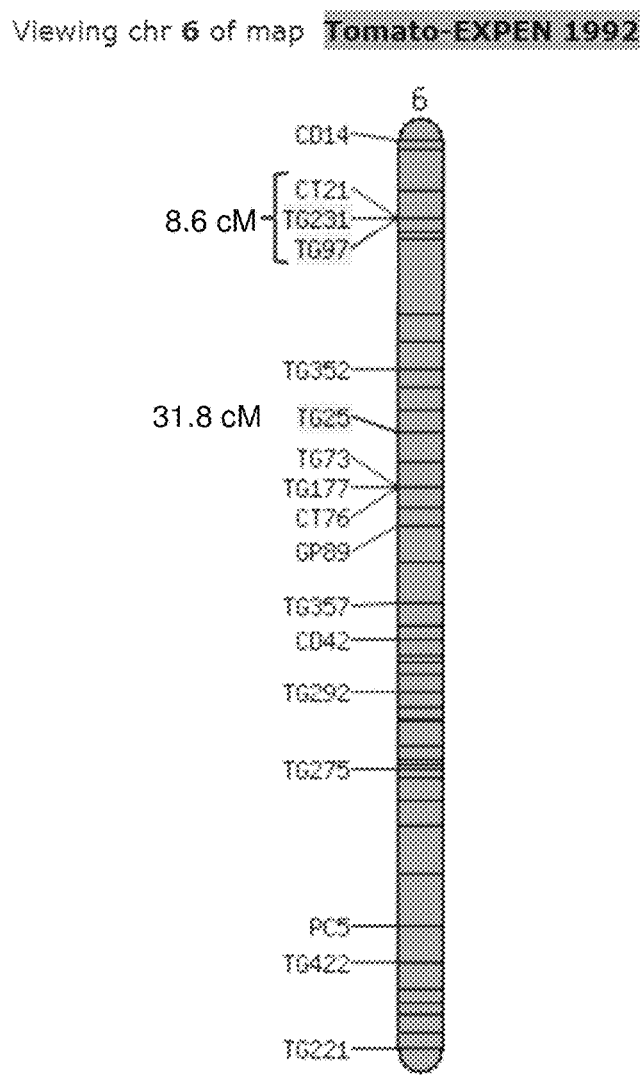
Figure 10. Map of chromosome 6 of Tomato-EXPEN 1992.

TOMATO YELLOW LEAF CURL VIRUS RESISTANCE

CROSS-REFERENCE TO PRIOR APPLICATIONS

This application is a National Stage of PCT/NL2012/050149, filed Mar. 12, 2012, and designating the United States (published in English on Sep. 20, 2012, as WO 2012/125025 A1), which claims priority under 35 U.S.C. § 119 to NL 2006378, filed Mar. 11, 2011, each hereby expressly incorporated by reference in its entirety and each assigned to the assignee hereof.

SEQUENCE LISTING

The instant application contains a Sequence Listing which has been submitted electronically in ASCII format and is hereby incorporated by reference in its entirety. Said ASCII copy, created on Sep. 19, 2014, is named 10022135-0001_SequenceListing.txt and is 44,106 bytes in size.

The invention relates to the field of plant biotechnology, more specifically to plant pathogen resistance. In particular, the application relates to the resistance to tomato yellow leaf curl virus (TYLCV).

Tomato yellow leaf curl disease, a devastating disease of tomato is caused by a complex of begomoviruses (genus *Begomovirus* within the Geminiviridae), generally being referred to as tomato yellow leaf curl virus (TYLCV). Whereas most begomoviruses contain a bi-partite, circular, single-stranded DNA genome, TYLCV only contains one circular ssDNA of about 2.7-2.8 Kb. Its genome contains six partially overlapping open reading frames that are bi-directionally organized and separated by an Intergenic Region (IR) of approximately 200 nucleotides (Gronenborn, B., 2007. The tomato yellow leaf curl virus genome and functions of its proteins. In: Czosnek, H. (Ed.), The Tomato Yellow Leaf Curl Virus Disease: Management, Molecular Biology and Breeding for Resistance. Springer, The Netherlands, pp. 67-84). Geminiviruses easily recombine during mixed infections, which not only leads to new variants and diversifications within the TYLCV cluster, but also makes it taxonomic classification more and more complex (Garcia-Andrés, S. et al., 2009, Virus Res. Doi:10.1016/j.virusres.2009.08.012; Monci, F. et al., 2002, Virology 303: 317-326; Garcia-Andrés, S. et al., 2007, Virology 365:210-219).

TYCLV is widespread in warm and (sub)tropical regions worldwide and is a limiting factor for tomato production in many regions (Cohen, S., Lapifot, M, 2007. Appearance and expansion of TYLCV: a historical point of view. In: Czosnek, H. (Ed.), The Tomato Yellow Leaf Curl Virus Disease: Management, Molecular Biology and Breeding for Resistance. Springer, The Netherlands, pp. 3-12). The disease is still spreading with recent outbreaks reported in California, USA, in China and Hawaii. TYLCV infections lead to stunting, yellowing, leaf curling and flower abortion. When plants are infected at a young stage, crop losses up to 100% may occur (Varma A., Malathi V. G., 2003. Annals of Applied Biology 142:145-164). The virus has a large host range, including many economically important crops like tomato, tobacco, pepper and potato (Polston J. E., Anderson P. K., 1997. Plant Disease 81=1358-1369), and is transmitted by the whitefly *Bemisia tabaci*. Besides being the insect vector of begomoviruses, whiteflies are pest insects due to their feeding damage on various crops.

Disease management of TYLCV is difficult because the whitefly insect vector is hard to control. The latter is often based on application of insecticides combined with physical barriers like polyethylene sheets or large plants like sorghum. Disadvantages of this management strategy are the large costs and labour involved. More importantly, whitefly insecticide resistance has meanwhile been reported (Horowitz, A. R, et al., 2007. Resistance of the TYLCV whitefly vector *Bemisia tabaci* to insecticides. In: Czosnek, H. (Ed.), The Tomato Yellow Leaf Curl Virus Disease: Management, Molecular Biology and Breeding for Resistance. Springer, The Netherlands, pp. 309-329), which stresses the importance of alternative management strategies.

One more durable strategy is to breed tomato cultivars (or other host plants) for resistance to TYLCV. Whereas domesticated tomato (*Solanum lycopersicum*) is susceptible to TYLCV, high levels of resistance were found in several wild tomato species, such as *S. pimpinellifolium*, *S. peruvianum*, *S. chilense*, *S. habrochaites* and *S. cheesmaniae* (Ji. Y. et al., 2007. Sources of resistance, inheritance and location of genetic loci conferring resistance to members of tomato-infecting begomoviruses. In: Czosnek, H. (Ed.), The Tomato Yellow Leaf Curl Virus Disease: Management, Molecular Biology and Breeding for Resistance. Springer, The Netherlands, pp. 343-362). Some of these have been used for intensive genetic studies which so far lead to the mapping of five TYLCV resistance genes (Table 1).

TABLE 1

Mapped TYLCV resistance genes

| | Genetic source | | | |
|---|---|---|---|---|
| | Accession/Line[a] | Species | Chromosome | Reference |
| Ty-1 | LA1969 | *S. chilense* | 6 (around the centromere) | {Zamir, 1994} |
| Ty-2 | B6013 | *S. habrochaites* | 11 | {Hanson et al., 2006. Rept. Tomato Genetic Cooperative 56: 17-18} |
| Ty-3 | LA2779 | *S. chilense* | 6 (on the long arm) | {Ji, 2007} |
| Ty-4 | LA1932 | *S. chilense* | 3 | {Ji et at., 2009. HortScience 44(3): 614-618} |
| Ty-5 | TY172 | *S. peruvianum* | 4 | {Anbinder et al., 2009. Theor Appl Genet 119: 519-530} |

[a]Source of Ty-5 gene was the tomato breeding line TY172, which is derived from 4 different accessions of *S. peruvianum*.

The Ty-1 gene, originating from *S. chilense* LA1969, was the first mapped TYLCV tolerance gene (Zamir, D. et al., 1994, Theor. Appl. Gen. 88:141-146). The authors preferred the term tolerance gene because homozygous Ty-1 plants challenged with TYLCV could develop mild disease symptoms, and only low virus titers were detected. In the present application, for uniformity, Ty-1 and Ty-3 are referred to as resistance genes. In many (commercial) breeding programs worldwide, Ty-1 has been introgressed into cultivated tomatoes. Though cultivars containing this resistance are for sale on the market (Ji, 2007), growers have encountered problems related to undesired agronomic traits (e.g. auto-necrosis) that are coupled with Ty-1 (personal communication with two breeders), a phenomenon that is known as linkage drag. Ty-1 was first mapped around the centromere of tomato chromosome 6 (Zamir, 1994). Follow up studies on newly developed molecular markers tightly linked to Ty-1, presented contradictory results on the genetic position of the Ty-1 locus. In one study Ty-1 was linked to the REX-1 locus within the Mi-1 gene cluster, suggesting that Ty-1 is located on the short arm of chromosome 6 (Milo, J. 2001. The PCR-based marker REX-1, linked to the gene Mi, can be used as a marker to TYLCV tolerance, in Proceedings of Tomato Breeders Roundtable, Antigua, Guatemala). In another study, Perez de Castro et al. (Perez de Castro, A. et al. 2007, J. Phytopath. 155:236-240) reported linkage of that Ty-1 to marker CT21 which is located below the centromere on the long arm (Table 2). So far, the exact position has not been elucidated and the underlying genetic information remains unknown. Within populations derived from interspecific crosses between S. lycopersicum and S. peruvianum (Seah, S. et al., 2004, Theor. Appl. Genet. 108:1635-1642; Bai Y. and Lindhout, P., 2004, Genetics, 168:1563-1573), suppression of recombination has been reported for the chromosomal region containing Mi-1. Since one study reported linkage of Ty-1 to the Mi-1 gene (Milo, 2001), the failure in fine-mapping Ty-1 as well as in reducing the introgression size in breeding programs is likely due to the suppression of recombination in this region. Although the causes for this suppression are not known, the location of a target-gene in heterochromatin regions around the centromere and/or chromosomal rearrangement(s) between cultivated and wild tomatoes may play a role in this.

There is thus need for more knowledge about the locus that provides resistance to TYLCV.

SUMMARY OF THE INVENTION

The present inventors now have discovered new markers for detecting the locus for Ty-1, which can be used for detecting whether a plant possesses the resistance gene. Such a detection method is very useful for breeding plants like tomato, tobacco, pepper and potato.

Further, the use of these new markers enabled elucidation of the genetic information underlying the Ty-1 resistance.

The present invention relates to molecular markers for determining the presence or absence of a gene conferring resistance to tomato yellow leaf curl virus from S. chilense (Ty-1) in a host plant, said host plant resulting from introgression of Ty-1 into a TYLCV-susceptible plant, whereby the marker is located between markers Msc09983-6 and M005H10 on chromosome 6.

Said marker is preferably a molecular marker selected from a restriction fragment length polymorphism (RFLP) marker, an amplified fragment length polymorphism (AFLP) marker, a single nucleotide polymorphism (SNP), a microsatellite marker, a sequence-characterized amplified region (SCAR) marker, a cleaved amplified polymorphic sequence (CAPS) marker, an isozyme marker, or any combination of these markers.

A preferred marker is located between markers M067G18-1 and Msc05732-18. Most preferred markers are selected from the CAPS markers Msc05732-4, cLEG-31-P16, and/or Msc05732-14, as depicted in Table 2.

Said TYLCV-susceptible plant is preferably selected from tomato, tobacco, pepper and potato. A preferred TYLCV-susceptible plant is provided by tomato (S. lycopersicum).

The invention further relates to the use of a molecular marker according to the invention for determining the presence or absence of a gene conferring resistance to tomato yellow leaf curl virus from S. chilense (Ty-1) in a host plant.

The invention further relates to methods for producing a host plant comprising a gene conferring resistance to tomato yellow leaf curl virus from S. chilense (Ty-1), the method comprising the steps of:

(a) introgressing genetic material from S. chilense into a TYLCV-susceptible plant to produce a host plant that comprises genetic material from S. chilense;

(b) analysing said host plant for the presence of the Ty-1 resistance allele with a marker according to the invention as detailed herein above; and (c) selecting one or more host plants comprising said resistance allele of S. chilense.

A method of the invention preferably additionally comprises determining whether the tomato plant is homozygous or heterozygous for the Ty-1 resistance allele of S. chilense.

A preferred TYLCV-susceptible plant in a method of the invention is S. lycopersicum.

The present invention additionally relates to a plant, or a part of a plant, that is obtainable by a method according to the invention. A preferred plant according to the invention is a tomato plant. Tomato fruits and tomato seed are preferred part of a tomato plant.

LEGENDS TO THE FIGURES

FIG. 1. MM (A), a susceptible $F_2$ plant (B) and a resistant F2 plant (C). Photos were taken two weeks after TYLCV infection. Clear TYLCV symptoms (yellow and curly leaves) are visible in MM and the susceptible $F_2$ plant.

Figure 2:
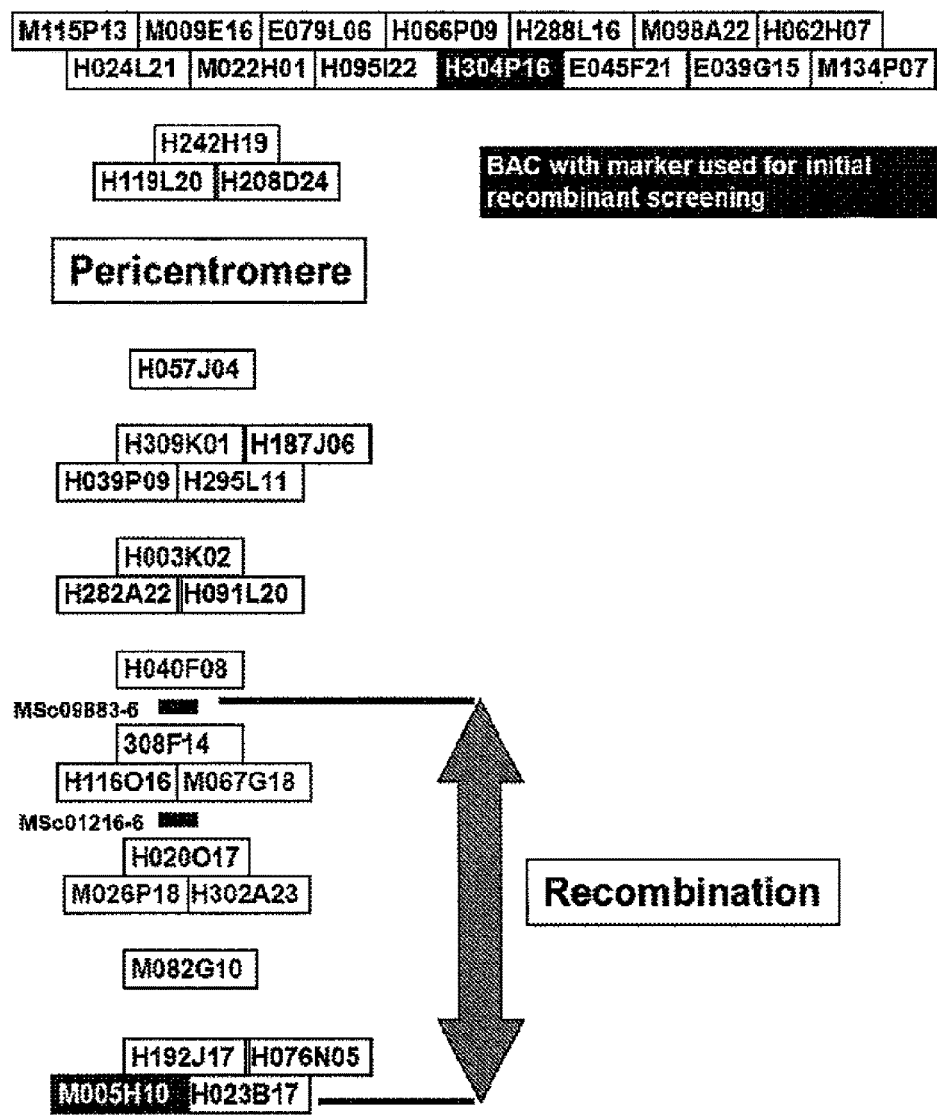

FIG. 2. Physical map of the Ty-1 region on chromosome 6 based on FISH experiments (Peters et al. 2009. Plant J. 58: 857-69). The following BACs were used for marker development: H304P16*, H242H19*, H119L20, H208D24, H057J04, H039P09, H309K01*, H295L11*, H187J06, H091L20, H040F08*, H116O16, H308F14, M067G18*, M026P18*, H302A23*, M082G10*, and M005H10*. The BACs marked with a star were successfully converted into a CAPS marker (see Table 3 for details). The grey arrow indicates the region with recombination events.

Figure 3:
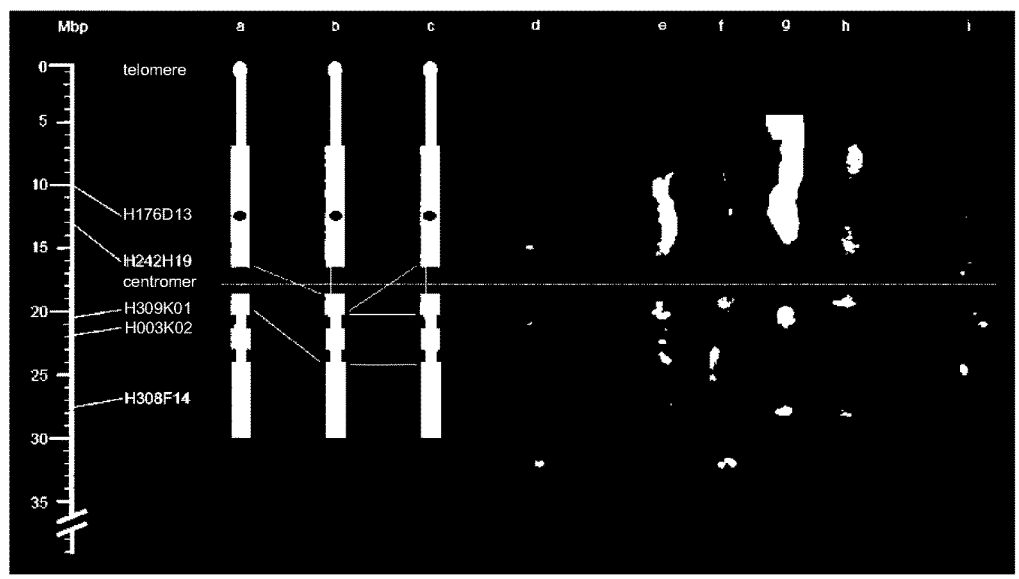

FIG. 3. BAC-FISH images and the schematic drawing of five BACs on pachytene chromosomes of F2 plants selected from population 1. BAC 242H19 is located above the centromere in 'a' plants (a) and below the centromere in 'b' plants (b); inverted order of BAC 309K01 and 003K02 between 'a' and 'b' plants (a and b); and multiple signals of BAC H242H19, H309K01 and H003K02 in 'h' plants (c). a, d) F2 plants homozygous for S. lycopersicum alleles in the S. chilense introgression; b, e, f, g, h) F2 plants homozygous for S. chilense alleles in the S. chilense introgression; c, i) F2 plants heterozygous in the S. chilense introgression.

Figure 4:
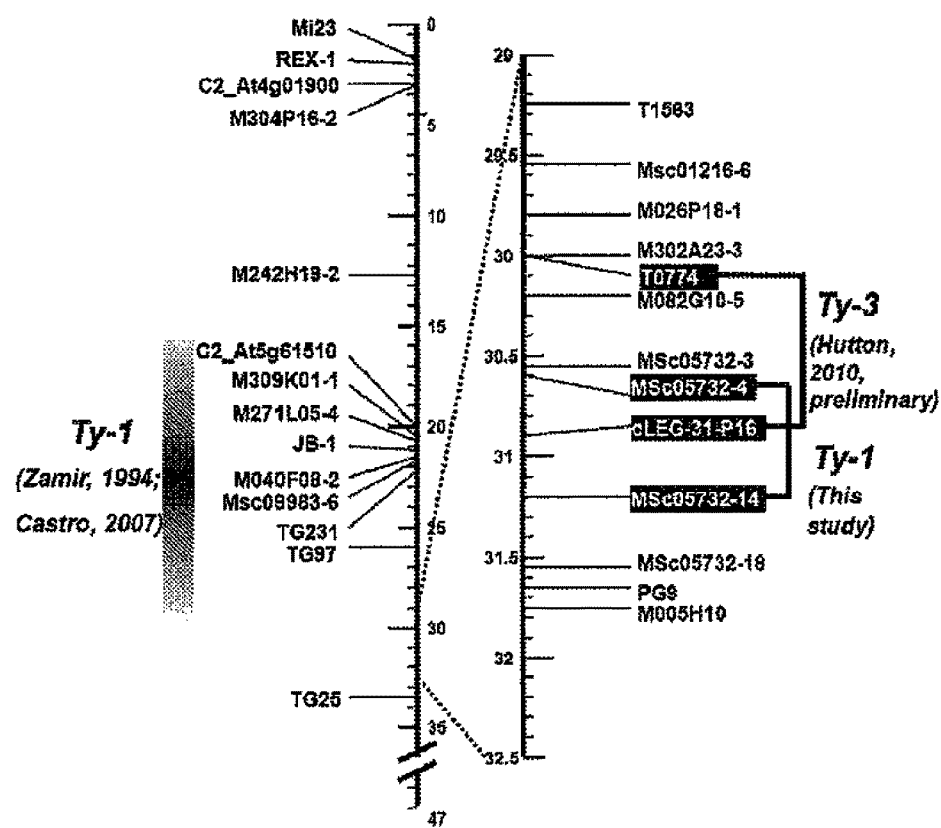

FIG. 4. Schematic physical maps of the short arm, the centromere and a part of the long arm of chromosome 6. Numbers given represent millions of basepairs. The position of the markers was based on Basic Local Alignment Search Tool (BLAST)® results on the Tomato WGS 2.31 Chromosomes database.

Figure 5:
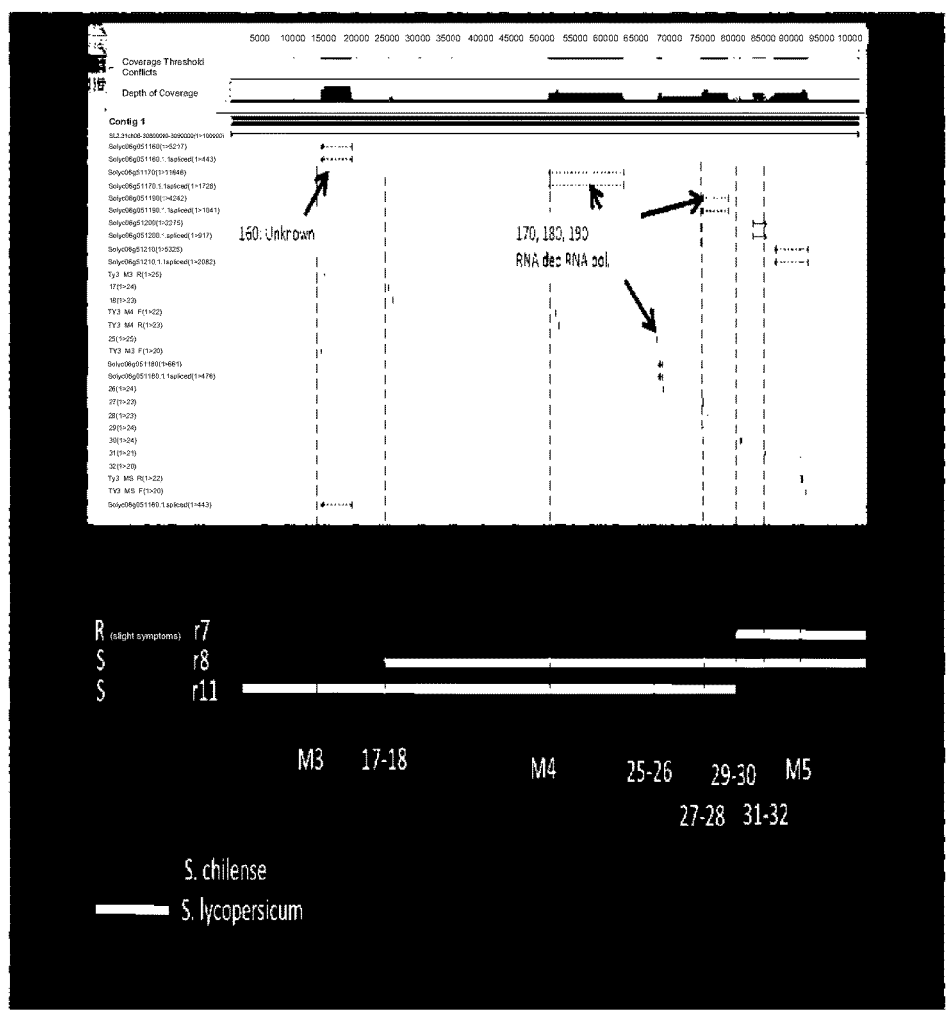

FIG. 5. Predicted genes in the region of interest are indicated with arrows and boxes. Marker positions are indicated with lines. The geneotype of three informative recombinants is indicated below the white box. It is visible that R7 has its recombination inside a predicted gene.

Figure 6:
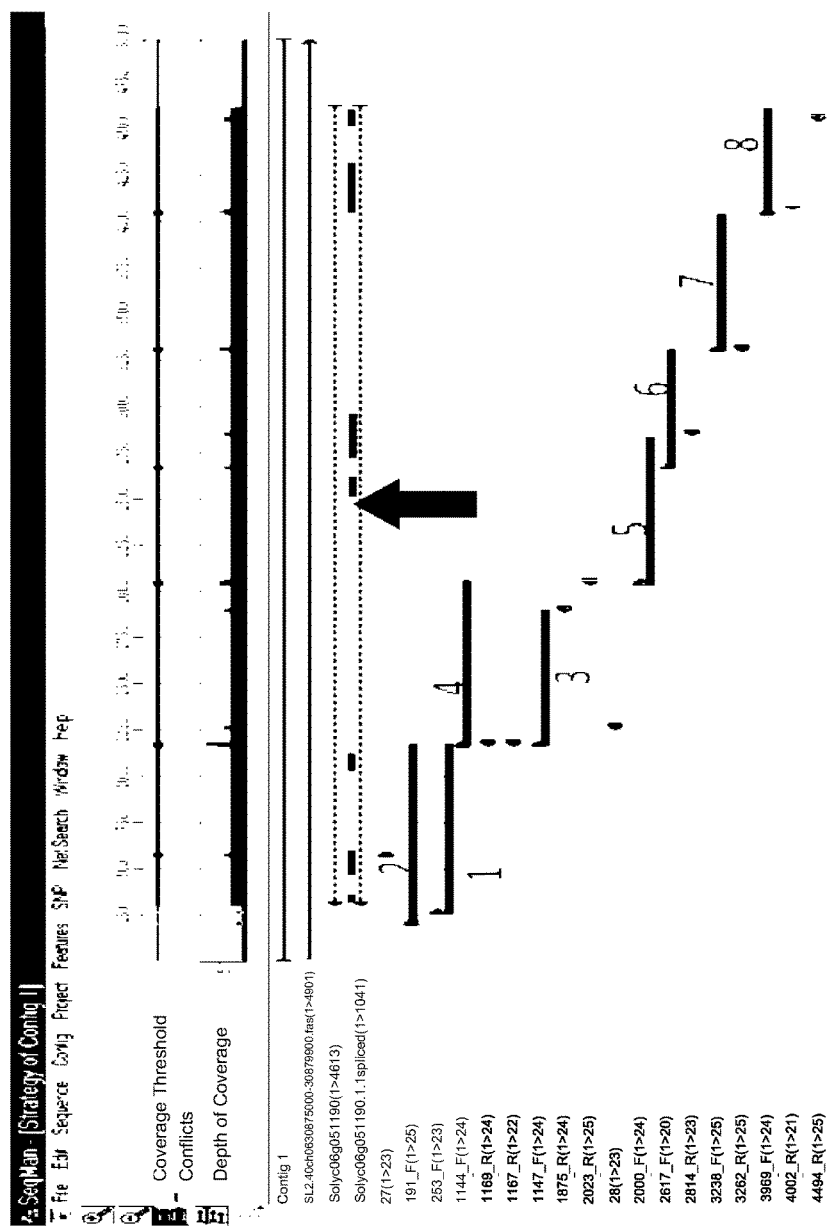

FIG. 6. Zoomed in picture of gene Solyc06g51190. Exons are depicted in red. The start codon is at the right. Amplification of fragments 1, 3, 5 and 6 was successful in all lines. It appears that in susceptible plants the first two exons cannot be amplified. After further analysis it was found that the recombination point in R7 is in fragment number 5, indicated by the large arrow.

FIG. 7. Gene sequence of the Ty-1 gene of *S. chilense* (SEQ ID NO: 1) and comparison with the corresponding sequence in a susceptible *S. lycopersicum* cv. Moneymaker tomato (SEQ ID NO:3). Note the deletion shortly after the transcription initiation site.

Next to this deletion/insertion sequence, the start ands top codons and all single nucleotide difference have been highlighted. For these latter the darker highlight indicates that the SNP has an effect on the amino acid encoded by the nucleotide sequence.

Figure 8:

FIG. 8. Silencing of RNA-dependent RNA polymerase (RDR) compromises Ty-1 conferred resistance. The Ty-1 plants infiltrated with TRV empty vector (left), and TRV vectors which silence RDRs Solyc06g051180 (middle) and Solyc06g051190 (right). Note: Solyc06g051180 and Solyc06g051190 belong to one RDR gene.

FIG. 9. Positions of various markers on SL2.5ch06.

FIG. 10. Map of chromosome 6 of Tomato-EXPEN 1992.

DETAILED DESCRIPTION OF THE INVENTION

Definitions

As used herein, the term "tomato yellow leaf curl virus (TYLCV)" refers to a virus from the genus *Begomovirus* within the Geminiviridae. TYLCV is a monopartite *begomovirus* that is primarily transmitted by the sweetpotato whitefly (*Bemisia tabaci*) and the biotype B (or silverleaf) whitefly (*Bemisia argentifolii*).

As used herein, the term "allele(s)" means any of one or more alternative forms of a gene, all of which alleles relate to at least one trait or characteristic. In a diploid cell or organism, the two alleles of a given gene occupy corresponding loci on a pair of homologous chromosomes. The present invention relates to molecular markers for determining the presence or absence of an allele, i.e. to genomic regions that may comprise one or more genes, but also regulatory sequences, it is in some instances more accurate to refer to "haplotype" (i.e. an allele of a chromosomal segment) in stead of "allele". However, in those instances, the term "allele" should be understood to comprise the term "haplotype".

A "gene" is defined herein as a hereditary unit consisting of a sequence of DNA that occupies a specific location on a chromosome and that contains the genetic instruction for a particular characteristics or trait in an organism.

A "locus" is defined herein as the position that a given gene occupies on a chromosome of a given species.

As used herein, the term "heterozygous" means a genetic condition existing when different alleles reside at corresponding loci on homologous chromosomes.

As used herein, the term "homozygous" means a genetic condition existing when identical alleles reside at corresponding loci on homologous chromosomes.

As used herein, the term "hybrid" means any offspring of a cross between two genetically unlike individuals, including but not limited to the cross between two inbred lines.

As used herein, the term "inbred" means a substantially homozygous individual or line.

In this application a "recombination event" is understood to mean a meiotic crossing-over.

As used herein, the terms "introgression", "introgressed" and "introgressing" refer to both a natural and artificial process whereby genes of one species, variety or cultivar are moved into the genome of another species, variety or cultivar, by crossing those species.

"Genetic engineering" and "transformation" are used herein as synonyms for the transfer of isolated and cloned genes into the DNA, usually the chromosomal DNA or genome, of another organism.

As used herein, the term "molecular marker" refers to an indicator that is used in methods for visualizing differences in characteristics of nucleic acid sequences, such as the presence of absence of a specific allele. Examples of molecular markers are restriction fragment length polymorphism (RFLP) markers, amplified fragment length polymorphism (AFLP) markers, single nucleotide polymorphisms (SNPs), microsatellite markers (e.g. SSRs), sequence-characterized amplified region (SCAR) markers, cleaved amplified polymorphic sequence (CAPS) markers or isozyme markers or combinations of the markers described herein which defines a specific genetic and chromosomal location.

The terms "resistant" and "resistance" encompass both partial and full resistance to infection. A TYLCV-susceptible plant may either be non-resistant or have low levels of resistance to infection by TYLCV.

The term "TYLCV-susceptible plant" refers to a plant such as tomato, tobacco, pepper and potato that is susceptible to infection by TYLCV. A preferred TYLCV-susceptible plant is tomato (*S. lycopersicum*). A TYLCV-susceptible plant may be a hybrid plant or an inbred plant such as a variety or a cultivar. A "TYLCV-susceptible plant" may be a commercially interesting plant.

The term "host plant" refers to a TYLCV-susceptible plant into which genetic material from *S. chilense* has been introduced by introgression and/or genetic engineering.

As used herein, the term "plant part" indicates a part of a plant, including single cells and cell tissues such as plant cells that are intact in plants, cell clumps and tissue cultures from which plants can be regenerated. Examples of plant parts include, but are not limited to, single cells and tissues from pollen, ovules, leaves, embryos, roots, root tips, anthers, flowers, fruits, stems shoots, and seeds; as well as pollen, ovules, leaves, embryos, roots, root tips, anthers, flowers, fruits, stems, shoots, scions, rootstocks, seeds, protoplasts, callus, and the like.

As used herein, the term "tomato plant" means any plant, line or population of *S. lycopersicum*, including tomato plants that result from introgression of genetic material from wild type tomato plants such as, for example, *S. pimpinellifolium, S. peruvianum, S. habrochaites, S. cheesmaniae* and/or *S. chilense* into *S. lycopersicum*.

As used herein, the term "variety" or "cultivar" means a group of similar plants that by structural or genetic features and/or performance can be distinguished from other varieties within the same species.

Identification of Molecular Markers Associated with Resistance to Tomato Yellow Leaf Curl Virus in *S. Chilense*

It is known that high levels of resistance to infection with TYLCV are present in several wild tomato species, such as *S. pimpinellifolium, S peruvianum, S. chilense, S. habrochaites* and *S. cheesmaniae* (Ji, 2007; ibid. The Ty-1 gene, originating from *S. chilense* LA1969, was the first mapped TYLCV-resistance gene (Zamir, 1994; ibid). However, the precise localization of the gene is not known and contradictory results on the genetic position of the Ty-1 locus have been obtained. So far, the exact position has not been elucidated and the underlying gene remains unknown. In addition, growers have encountered problems related to linkage drag resulting from a large introgression size in breeding programs, as the presently known markers are not tightly linked to the Ty-1 locus. Suppression of recombination has been documented for the chromosomal region that was reported to contain the Ty-1 locus, which may have contributed to the failure in fine-mapping of Ty-1 as well as in reducing the introgression size in breeding programs.

Molecular markers are used for the visualisation of differences in parental nucleic acid sequences. This visualisation is possible due to DNA-DNA hybridisation techniques (RFLP) and/or due to techniques using the polymerase chain reaction (e.g. CAPS marker, STS, microsatellites, AFLP). All differences between two parental genotypes will segregate in a hybrid population based on the cross of these parental genotypes. The segregation of the different markers may be compared and recombination frequencies can be calculated. The recombination frequency of molecular markers on different chromosomes is generally 50%. Between molecular markers located on the same chromosome the recombination frequency depends on the distance between the markers. A low recombination frequency corresponds to a low distance between markers on a chromosome. Comparing all recombination frequencies will result in the most logical order of the molecular markers on the chromosomes, termed a linkage map. A group of adjacent or contiguous markers on the linkage map that is associated with resistance to TYLCV-infection pinpoints to the position of the TYLCV resistance gene.

Upon the identification of a marker, the resistance may for instance be confirmed by assessing TYLCV-resistance in progenies segregating for the markers under investigation. The assessment of the TYLCV resistance may suitably be performed by TYLCV inoculation using viruliferous whiteflies or by agroinoculation using *Agrobacterium tumefaciens* as described herein.

An aspect of the present invention is provided by molecular markers for resistance against TYLCV in plants, especially markers for the Ty-1 resistance gene of *S. chilense*. A characteristic of such molecular markers is that, when present in plants, they are indicative of the presence of resistance to infection with TYLCV upon contacting said plant with infective amount of TYLCV material.

The inventors surprisingly found that the genomic region where Ty-1 is located between markers Msc09983-6 and M005H10 on the long arm of chromosome 6 (see FIG. 4). Therefore, any marker located within that region may be used to assess the presence of Ty-1 in the genome of a plant. The indicated genomic region does not include the markers REX-1 and JB-1, which were previously reported to be linked to the Ty-1 locus. The indicated genomic region neither encompasses the chromosomal region in which recombination has been documented to be suppressed (Seah et al., 2004, ibid; Bai and Lindhout, 2004, ibid). More specifically it has been found that Ty-1 is located between markers MSc05732-4 and MSC5732-14 and even more specifically between Ty3-M3 and Ty3-M5.

The invention therefore provides a molecular marker for determining the presence or absence of Ty-1 in a host plant, said host plant resulting from introgression of the Ty-1 gene from *S. chilense* into a TYLCV-susceptible plant, whereby the marker is located between markers Msc09983-6 and M005H10, more preferably between markers MSc05732-4 and MSC5732-14 and even more preferably between Ty3-M3 and Ty3-M5 on chromosome 6 of *S. chilense*. A molecular marker according to the invention enables to determine whether the chromosomal nucleic acid between markers Msc09983-6 and M005H10, more preferably between markers MSc05732-4 and MSC5732-14 and even more preferably between Ty3-M3 and Ty3-M5on chromosome 6 is from *S. chilense* or from the TYLCV-susceptible plant, thereby indicating the presence of absence of the Ty-1 gene from *S. chilense*.

The detection of the presence or absence of a molecular marker according to the invention comprises detecting the presence or absence of a nucleic acid molecule encompassing said marker in a plant. The nucleic acid molecule may be detected by methods known to the skilled person. For instance, a nucleic acid molecule comprising a marker of the invention may be isolated from a plant by fragmenting the genome of said plant and selecting those fragments harboring one or more of the molecular markers. Subsequently, or alternatively, the marker sequences (or parts thereof) are amplified from a genomic nucleic acid sample or a genome fragment obtained from said plant. The amplified nucleic acid may then be purified in order to obtain the isolated marker. The nucleotide sequence of the marker(s) comprised on the isolated nucleic acid may then be obtained by standard sequencing methods.

A marker according to the invention is preferably selected from a restriction fragment length polymorphism (RFLP) marker, an amplified fragment length polymorphism (AFLP) marker, a single nucleotide polymorphism (SNP), a microsatellite marker, a sequence-characterized amplified region (SCAR) marker, a cleaved amplified polymorphic sequence (CAPS) marker, an isozyme marker, or any combination of these markers, provided that the marker is present in the chromosomal location between markers Msc09983-6 and M005H10, more preferably between markers MSc05732-4 and MSC5732-14 and even more preferably between Ty3-M3 and Ty3-M5 on chromosome 6 of *S. chilense* and enables to determine whether the chromosomal nucleic acid between the markers Msc09983-6 and M005H10, more preferably between markers MSc05732-4 and MSC5732-14 and even more preferably between Ty3-M3 and Ty3-M5 is from *S. chilense* or from a TYLCV-susceptible plant.

In one embodiment, a molecular marker according to the invention comprises a polymorphism such as, for example, a SNP between the chromosomal nucleic acid of *S. chilense* and chromosomal nucleic acid of the TYLCV-susceptible plant. Methods to detect a polymorphism are known in the art and comprise the steps of providing an oligonucleotide or a polynucleotide capable of hybridizing under stringent hybridization conditions to a nucleic acid sequence of the molecular marker, and determining the presence of specific hybridization of said oligonucleotide or polynucleotide to said genomic nucleic acid. Preferably said method is performed on a nucleic acid sample obtained from said host plant, although in situ hybridization methods may also be employed.

The phrase "stringent hybridization conditions" refers to conditions under which a probe or polynucleotide will hybridize to its target subsequence, typically in a complex mixture of nucleic acids, but to essentially no other sequences. Stringent conditions are sequence-dependent and will be different in different circumstances. Longer sequences hybridize specifically at higher temperatures. An extensive guide to the hybridization of nucleic acids is found in Tijssen (Thijssen, 1993. In: "Laboratory Techniques in Biochemistry and Molecular Biology". Elsevier). Generally, stringent conditions are selected to be about 5-10° C. lower than the thermal melting point (Tm) for the specific sequence at a defined ionic strength and pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions are often: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length.

As used herein, oligonucleotides are typically from about 7, 8, 9, 10, 12, 15, 18 20 25, 30, 40, 50 or up to about 100 nucleotides in length. Nucleic acids and polynucleotides are polymers of more than 100 nucleotides, such as 200, 300, 500, 1000, 2000, 3000, 5000, 7000, 10.000 nucleotides.

A preferred method for detection of the presence or absence of a molecular marker uses amplification and a restriction endonuclease. CAPS markers allow the detection of single nucleotide polymorphisms. The CAPS technique is a preferred marker system for marker-assisted selection. A preferred CAPS molecular marker according to the invention is selected from the CAPS markers Msc09983-6, M067G18-1, Msc01216-6, M026P18-1, M302A23-3, M082G10-5, Msc05732-3, Msc05732-4, cLEG-31-P16, Msc05732-14, Msc05732-18, Ty3-M3, Ty3-M5 and M005H10, as indicated in FIG. 4.

A more preferred molecular marker according to the invention resides on the long arm of chromosome 6, more specifically in the region between 27.2 cM and 33.7 cM on the long arm of chromosome 6, between markers M067G18-1 and Msc05732-18, and is selected from M067G18-1, Msc01216-6, M026P18-1, M302A23-3, M082G10-5, Msc05732-3, Msc05732-4, cLEG-31-P16, Msc05732-14, Ty3-M3, Ty3-M5 and Msc05732-18.

A most preferred molecular marker according to the invention is selected from Msc05732-4, Ty3-M3 and Ty3-M5 and Msc05732-14.

The markers provided by the present invention are closely linked to the Ty-1 gene from S. chilense. Because of this close linkage, the markers according to the invention may suitably be used for detecting the presence of one or more TYLCV-resistance genes in other wild type tomato plants such as, for example, S. pimpinellifolium, S. peruvianum, S. habrochaites and S. cheesmaniae. Therefore, the invention further provides a molecular marker for determining the presence or absence of a gene conferring resistance to Ty-1 in a host plant, said host plant resulting from introgression of a TYLCV-resistance gene from a wild type tomato plant into a TYLCV-susceptible plant, whereby the marker is located between markers Msc09983-6 and M005H10, more preferably between markers MSc05732-4 and MSC5732-14 and even more preferably between Ty3-M3 and Ty3-M5on chromosome 6 of S. chilense.

A molecular marker according to the invention may be used for determining the presence or absence of Ty-1 from S. chilense in a host plant, resulting from introgression of the Ty-1 gene into a TYLCV-susceptible plant. A preferred TYLCV-susceptible plant according to the invention is S. lycopersicum, more preferred a commercially attractive inbred plant such as a variety or a cultivar such as, for example, S. lycopersicon cv. Moneymaker The invention further provides the use of a molecular marker according to the invention for determining the presence or absence of Ty-1 from S. chilense in a host plant.

In the region of interest, between the markers Ty3-M3 and Ty3-M5 four putative genes are available as candidate for the genetic source of the resistance, Solyc06g51160, Solyc06g51170, Solyc06g51180 and Solyc06g51190. It appears from further studies as shown in the experimental part that the three latter three genes (Solyc06g51170, Solyc06g51180 and Solyc06g51190), are actually one gene (alternatively called Ty-1 in the present invention) that is responsible for the resistance. Its sequence is given in FIG. 7.

First of all, this means that the TYLCV resistance is confined to one gene, which would facilitate transgenic approaches. Secondly, it enables to pinpoint the cause of the resistance and/or sensitivity. Where this cause has a genetic basis, the underlying presence or absence of nucleotide sequences can provide further markers for establishing the presence or absence of the resistance. Basically any nucleotide sequence or SNP (single neucleotide polymorphism) that is characteristic for the resistance and in this case which is specific for the presence of a functionally active Ty-1 gene can be applied as a marker. Further, not only on nucleotide level (DNA, (m)RNA) but also on the peptide level, i.e. the protein encoded by Ty-1, can serve as a marker for the resistance. In any case, plants that have a sufficient level of the protein encoded by Ty-1 are deemed to be TYLCV-resistant plants. Plants that have a less than normal level (wherein the normal level is defined as the level that is present in a tomato plant having a functional Ty-1 gene) of the protein are deemed to be TYLCV-susceptible.

The Ty-1 gene is coding for a RNA-dependent RNA polymerase (RDR). As a matter of fact three out of the four predicted genes in the interval between markers Ty3-M3 and Ty3-M5 are coding one RDR gene, the fourth, Solyc06g51160 has an unknown function. As is shown in the experimental part, silencing of the RDR gene compromised the resistance conferred by Ty-1 and silencing of the gene with the unknown function had no effect (FIG. 8).

Comparison with known sequences reveals that Ty-1 is a RDR3/RDR4/RDR5 homolog. In Arabidopsis six RDR genes have been identified. The current Ty-1 gene resembles a group of three Arabidopsis RDR's that are characterized by having a typical catalytic DFDGD motif (SEQ ID NO: 68). This motif is also present in Ty-1. This is further the first time that a specific function for this class of RDRs has been described.

Accordingly, the present invention also comprises markers that are derived from the Ty-1 sequence. A comparison with the orthologous gene sequence in Moneymaker (see FIG. 7) reveals that the presence or absence of a stretch of 12 nucleotides is characteristic for the presence or absence of the functional gene. Accordingly, this nucleotide sequence CCTTCTTGTATA (SEQ ID NO: 67) would be very useful as marker for the presence of the resistance. Further, all the highlighted SNPs that can be observed in FIG. 7 would qualify as marker.

It will be clear to the skilled person that any method suitable for detecting a nucleotide change may be applied for determining presence or absence of the resistance gene. Methods for detecting a nucleotide change can utilize one or more oligonucleotide probes or primers that selectively hybridize to a target polynucleotide which contains the nucleotide sequence CCTTCTTGTATA (SEQ ID NO: 67) or one or more SNP positions or other markers. Such probes or primers include, for example, an amplification primer pair. Probes useful in practicing a method of the invention can include, for example, an oligonucleotide that is complementary to and spans a portion of the target polynucleotide, including the position of the marker, wherein the presence or absence of a specific nucleotide at the position (e.g, an SNP or an indel) is detected by the presence or absence of selective hybridization of the probe. Such a method can further include contacting the target polynucleotide and hybridized oligonucleotide with an endonuclease, and detecting the presence or absence of a cleavage product of the probe, depending on whether the nucleotide occurrence at the marker site is complementary to the corresponding nucleotide of the probe. A pair of probes that specifically hybridize upstream and adjacent and downstream and adjacent to the site of the marker, wherein one of the probes includes a nucleotide complementary to a nucleotide occurrence of the marker, also can be used in an oligonucleotide ligation assay, wherein the presence or absence of a ligation product is indicative of a specific nucleotide occurrence at the marker site. An oligonucleotide also can be useful as a primer, for example, for a primer extension reaction, wherein the product (or absence of a product) of the extension reaction is indicative of the nucleotide occurrence. In addition, a primer pair useful for amplifying a portion of the target polynucleotide including the marker site can be useful, wherein the amplification product is examined to determine the nucleotide occurrence at the marker site.

Where the particular nucleotide occurrence of a marker is such that the nucleotide occurrence results in an amino acid change in an encoded polypeptide, the nucleotide occurrence can be identified indirectly by detecting the particular amino acid in the polypeptide. The method for determining the amino acid will depend, for example, on the structure of the polypeptide or on the position of the amino acid in the polypeptide. Where the polypeptide contains only a single occurrence of an amino acid encoded by the particular polymorphism, the polypeptide can be examined for the presence or absence of the amino acid. For example, where the amino acid is at or near the amino terminus or the carboxy terminus of the polypeptide, simple sequencing of the terminal amino acids can be performed. Alternatively, the polypeptide can be treated with one or more enzymes and a peptide fragment containing the amino acid position of interest can be examined, for example, by sequencing the peptide, or by detecting a particular migration of the peptide following electrophoresis. Where the particular amino acid comprises an epitope of the polypeptide, the specific binding, or absence thereof, of an antibody specific for the epitope can be detected. Other methods for detecting a particular amino acid in a polypeptide or peptide fragment thereof are well known and can be selected based, for example, on convenience or availability of equipment such as a mass-spectrometer, capillary electrophoresis system, magnetic resonance imaging equipment, and the like.

The marker-assisted selection steps in the methods of the invention can in principle be performed by applying any nucleic acid amplification method, such as the Polymerase Chain Reaction (PCR; Mullis 1987, U.S. Pat. Nos. 4,683, 195, 4,683,202, en 4,800,159) or by using amplification reactions such as Ligase Chain Reaction (LCR; Barany 1991, Proc. Natl. Acad. Sci. USA 88:189-193; EP Appl. No., 320,308), Self-Sustained Sequence Replication (3SR; Guatelli et al., 1990, Proc. Natl. Acad. Sci. USA 87:1874-1878), Strand Displacement Amplification (SDA; U.S. Pat. Nos. 5,270,184, en 5,455,166), Transcriptional Amplification System (TAS; Kwoh et al., Proc. Natl. Acad. Sci. USA 86:1173-1177), Q-Beta Replicase (Lizardi et al., 1988, Bio/Technology 6:1197), Rolling Circle Amplification (RCA; U.S. Pat. No. 5,871,921), Nucleic Acid Sequence Based Amplification (NASBA), Cleavage Fragment Length Polymorphism (U.S. Pat. No. 5,719,028), Isothermal and Chimeric Primer-initiated Amplification of Nucleic Acid (ICAN), Ramification-extension Amplification Method (RAM; U.S. Pat. Nos. 5,719,028 and 5,942,391) or other suitable methods for amplification of DNA.

In order to amplify DNA with a small number of mismatches to one or more of the amplification primers, an amplification reaction may be performed under conditions of reduced stringency (e.g. a PCR amplification using an annealing temperature of 38° C., or the presence of 3.5 mM $MgCl_2$). The person skilled in the art will be able to select conditions of suitable stringency.

The detection of the amplification products in principle can be accomplished by any suitable method known in the art. The detection fragments may be directly stained or labeled with radioactive labels, antibodies, luminescent dyes, fluorescent dyes, or enzyme reagents. Direct DNA stains include for example intercalating dyes such as acridine orange, ethidium bromide, ethidium monoazide or Hoechst dyes.

Alternatively, the DNA fragments may be detected by incorporation of labeled dNTP bases into the synthesized DNA fragments. Detection labels which may be associated with nucleotide bases include e.g. fluorescein, cyanine dye or BrdU.

When using a probe-based detection system, a suitable detection procedure for use in the present invention may for example comprise an enzyme immunoassay (ETA) format. Probes useful for the detection of the target DNA as disclosed herein preferably bind only to at least a part of the DNA sequence region as amplified by the DNA amplification procedure. Those of skill in the art can prepare suitable probes for detection based on the nucleotide sequence of the target DNA without undue experimentation. Also the complementary sequences of the target DNA may suitably be used as detection probes in a method of the invention, provided that such a complementary strand is amplified in the amplification reaction employed.

Any suitable method for screening the nucleic acids of a plant or part thereof for the presence or absence of polymorphisms is considered to be part of the methods according to the invention. Such screening methods include, but are not limited to: DNA sequencing, restriction fragment length polymorphism (RFLP) analysis, amplified fragment length polymorphism (AFLP) analysis; heteroduplex analysis, single strand conformational polymorphism (SSCP) analysis, denaturing gradient gel electrophoresis (DGGE), real time PCR analysis (e.g. Taqman®), temperature gradient gel electrophoresis (TGGE), primer extension, allele-specific hybridization, and INVADER® genetic analysis assays, cleavage fragment length polymorphism (CFLP) analysis, sequence-characterized amplified region (SCAR) analysis, cleaved amplified polymorphic sequence (CAPS) analysis The development of primers and probes useful for the detection of polymorphic positions in a nucleic acid is within the realm of ordinary skill (see for instance Sambrook, J. et al., 2001).

By using standard DNA technology it is possible to produce probes and primers that directly or indirectly hybridize to the DNA samples to be tested or cDNA produced from RNA by reverse transcription, and which can be used in assays for the detection of the markers. Nucleic acid amplification techniques allow the amplification of fragments of nucleic acids, which may be present in very low amounts.

In order to develop nucleic acid-based detection methods, the SNP- or indel-specific sequences must be determined for which primers or probes may then be developed. To detect the SNPs or indels by nucleic acid amplification and/or probe hybridization, the nucleic acid may be isolated from any raw sample material, optionally reverse transcribed into cDNA and directly cloned and/or sequenced. DNA and RNA isolation kits are commercially available from for instance QIAGEN GmbH, Hilden, Germany, or Roche Diagnostics, a division of F. Hoffmann-La Roche Ltd, Basel, Switzerland. Nucleic acid-based detection of insertions or deletions can be accomplished accordingly.

A sample useful for practicing a method of the invention can be any biological sample from a plant or a part thereof that contains nucleic acid molecules, including portions of the chromosome sequences to be examined, or corresponding encoded polypeptides, depending on the particular method. As such, the sample can be a cell or tissue sample. As some of the markers may be located in a non-coding region, the nucleic acid sample can be a deoxyribonucleic acid (DNA) sample, particularly genomic DNA or an amplification product thereof. However, where hetero-nuclear ribonucleic acid (RNA), which includes unspliced mRNA precursor RNA molecules, is available, a cDNA or amplification product thereof can be used. The nucleic acid sample can thus be DNA or RNA, or products derived therefrom such as, for example, amplification products.

Using either the cloned nucleic acid as a hybridization probe, using sequence information derived from the clone, or by designing degenerative primers based on the sequence of the SNP and its flanking sequences, nucleic acid hybridization probes and/or nucleic acid amplification primers may be designed an used in a detection assay for detecting the SNPs and/or indels in a sample as defined herein.

The DNA, or alternatively, the cDNA may be PCR amplified by using for instance Pfu and Taq DNA polymerases and amplification primers specific for the SNP DNA sequences. Also complete commercially available systems may be used for PCR (e.g. available form various suppliers such as Roche Diagnostics). A suitable method may for instance include mixing into a suitable aqueous buffering system (e.g. a commercially available PCR buffer) a suitable amount of total DNA as a template (e.g. 1 to 5 µg), a suitable amount (e.g. 10 pmol) of a pair of bi-directional amplification primers, a suitable amount of dNTPs and the DNA polymerase, denaturing the nucleic acids by boiling for 1 min, and performing a cycling reaction of around 10-50 alternating cycles of stringent primer hybridization, strand elongation and denaturing, at suitable temperatures to obtain DNA copies of the DNA template as amplification product. The amount of copies produced upon a certain number of cycles correlates directly to the amount of target DNA in the DNA template.

The skilled person is well aware of the available quantitative PCR methods presently available from commercial suppliers to quantify the amount of target DNA in the template. The term "hybridization signal" as used herein inter alia refers to the amount of amplification product produced upon a certain number of cycles and thus to the amount of target DNA available as template in the reaction.

In order to amplify a nucleic acid with a small number of mismatches to one or more of the amplification primers, an amplification reaction may be performed under conditions of reduced stringency (e.g. a PCR amplification using an annealing temperature of 38° C., or the presence of 3.5 mM $MgCl_2$). The person skilled in the art will be able to select conditions of suitable stringency.

The primers herein are selected to be "substantially" complementary (i.e. at least 65%, more preferably at least 80% perfectly complementary) to their target regions present on the different strands of each specific sequence to be amplified. It is possible to use primer sequences containing e.g. inositol residues or ambiguous bases or even primers that contain one or more mismatches when compared to the target sequence. In general, sequences that exhibit at least 65%, more preferably at least 80% homology with the target DNA or RNA oligonucleotide sequences are considered suitable for use in a method of the present invention. Sequence mismatches are also not critical when using low stringency hybridization conditions.

The detection of the amplification products can in principle be accomplished by any suitable method known in the art. The amplified fragments may be directly stained or labeled with radioactive labels, antibodies, luminescent dyes, fluorescent dyes, or enzyme reagents. Direct DNA stains include for example intercalating dyes such as acridine orange, ethidium bromide, ethidium monoazide or Hoechst dyes.

Alternatively, the DNA or RNA fragments may be detected by incorporation of labeled dNTP bases into the synthesized fragments. Detection labels which may be associated with nucleotide bases include e.g. fluorescein, cyanine dye, digoxigenin (DIG) or bromodeoxyuridine (BrdU).

Other methods of analysing the nucleic acid suitably comprise the use of a primer extension assay; a Taqman® PCR; a differential hybridization assay; an assay which detects allele-specific enzyme cleavage; and/or allele-specific PCR.

When using a probe-based detection system, a suitable detection procedure for use in the present invention may for example comprise an enzyme immunoassay (ETA) format (Jacobs et al., 1997, J Clin Microbiol 35:791-795). For performing a detection by manner of the ETA procedure, either the forward or the reverse primer used in the amplification reaction may comprise a capturing group, such as a biotin group for immobilization of target DNA PCR amplicons on e.g. a streptavidin coated microtiter plate wells or streptavidin coated Dynabeads® (Dynal Biotech, Oslo, Norway) for subsequent EIA detection of target DNA amplicons. The skilled person will understand that other groups for immobilization of target DNA PCR amplicons in an ETA format may be employed.

Probes useful for the detection of the target nucleic acid sequences preferably bind only to at least a part of the Solyc06g51190 nucleic acid sequence region as amplified by the nucleic acid amplification procedure. Those of skill in the art can prepare suitable probes for detection based on the nucleotide sequence of the target nucleic acid without undue experimentation as set out herein. Also the complementary nucleotide sequences, whether DNA or RNA or chemically synthesized analogues, of the target nucleic acid may suitably be used as type-specific detection probes in a method of the invention, provided that such a complementary strand is amplified in the amplification reaction employed.

Suitable detection procedures for use herein may for example comprise immobilization of the amplicons and probing the nucleic acid sequences thereof by e.g. Northern and Southern blotting. Other formats may comprise an ETA format as described above. To facilitate the detection of binding, the specific amplicon detection probes may comprise a label moiety such as a fluorophore, a chromophore, an enzyme or a radio-label, so as to facilitate monitoring of binding of the probes to the reaction product of the amplification reaction. Such labels are well known to those skilled in the art and include, for example, fluorescein isothiocyanate (FITC), β-galactosidase, horseradish peroxidase, streptavidin, biotin, digoxigenin, $^{35}S$, $^{14}C$, $^{32}P$ or $^{125}I$. Other examples will be apparent to those skilled in the art.

Detection may also be performed by a so-called reverse line blot (RLB) assay, such as for instance described by Van den Brule et al. (2002). For this purpose RLB probes are preferably synthesized with a 5' amino group for subsequent immobilization on e.g. carboxyl coated nylon membranes. The advantage of an RLB format is the ease of the system and its speed, thus allowing for high throughput sample processing.

The use of nucleic acid probes for the detection of RNA or DNA fragments is well known in the art. Mostly these procedures comprise the hybridization of the target nucleic acid with the probe followed by post-hybridization washings. Specificity is typically the function of post-hybridization washes, the critical factors being the ionic strength and temperature of the final wash solution. For nucleic acid hybrids, the Tm can be approximated from the equation of Meinkoth and Wahl (1984): Tm=81.5° C.+16.6 (log M)+0.41 (% GC)−0.61 (% form)-500/L; where M is the molarity of monovalent cations, % GC is the percentage of guanosine and cytosine nucleotides in the nucleic acid, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, the hybridization and/or wash conditions can be adjusted to hybridize to sequences of the desired identity. For example, if sequences with >90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization anchor wash solutions are inherently described. If the desired degree of mismatching results in a Tm of less than 45° C. (aqueous solution) or 32° C. (formamide solution) it is preferred to increase the SSC concentration so that a higher temperature can be used. An extensive guide to the hybridization of nucleic acids is found in Tijssen, 1993 supra; Ausubel et al, 1998 supra.

Such detection methods can readily be applied for the purpose of selecting a plant of part thereof with TYLCV resistancy.

Production of TYLCV-Resistant Plants

In a further embodiment, the invention provides a method for producing a host plant comprising Ty-1 from *S. chilense*, the method comprising the steps of (a) introgressing genetic material from *S. chilense* into a TYLCV-susceptible plant to produce a host plant that comprises genetic material from *S. chilense*; (b) analysing said host plant for the presence of the resistance allele with a molecular marker according to the invention; and (c) selecting one or more host plants comprising said Ty-1 resistance allele of *S. chilense*, thus producing a host plant comprising Ty-1 from *S. chilense*.

A method according to the invention is preferably used to generate inbred plant lines, such as tomato plant lines, using the techniques of recurrent selection and backcrossing, selfing and/or dihaploids or any other technique used to make plant lines. In a preferred method, TYLCV-resistance is introgressed into a TYLCV-susceptible plant by crossing the TYLCV-susceptible plant with *S. chilense*. The TYLCV-susceptible plant is a plant that is non-resistant or has a low level of resistance to TYLCV and possesses commercially desirable characteristics such as, but not limited to, disease resistance, insect resistance, valuable fruit characteristics, etc. The progeny resulting from the cross between the TYLCV-susceptible plant and *S. chilense* are backcrossed to the TYLCV-susceptible plant. The resulting plant population is then screened for the presence of TYLCV-resistance. The population can be screened in a number of different ways, for example using TYLCV inoculation as described herein above.

A preferred method comprises one or more of the hereinbefore described molecular markers, including the SNP and/or indel nucleic acid markers, to identify those progeny that comprise Ty-1. A hybrid plant that comprises the requisite nucleic acid sequence encoding for TYLCV resistance, and possess commercially desirable characteristics, is then selected and selfed in order to provide for homozygous pure breeding progeny comprising Ty-1. The result of such breeding and selection is the production of lines that are genetically homogenous for Ty-1 as well as homozygous for other genes that are associated with traits of commercial interest.

A preferred method according to the invention further comprises determining whether the plant is homozygous or heterozygous for the TYLCV-resistance allele of *S. chilense*.

The TYLCV-resistant inbred lines described herein can be used in additional crossings to create TYLCV-resistant hybrid plants. For example, a first TYLCV-resistant inbred plant according to the invention is crossed with a second inbred plant possessing commercially desirable traits such as, but not limited to, disease resistance, insect resistance, desirable fruit characteristics, etc. This second inbred tomato line may or may not be TYLCV-resistant.

Based on the herein provided nucleic acid sequence of the Ty-1 gene, the invention also provides the means to introduce or increase resistance against TYLCV in a TYLCV susceptible plant.

A TYLCV-susceptible plant used as a recipient in the transformation process or used in a breeding method of the invention plant is preferably selected from breeding plants such as, but not limited to, tomato, tobacco, pepper and potato. Preferably, it is *S. lycopersicum*, more preferred a commercially attractive inbred plant such as a variety or a cultivar such as, for example, *S. lycopersicon* cv. Moneymaker.

The invention therefore also provides a method for providing at least partial resistance or increasing resistance in a plant against TYLCV infection comprising providing a TYLCV-susceptible plant or a part thereof with:

an isolated or recombinant nucleic acid sequence comprising a nucleic acid sequence encoding the protein encoded by the Ty-1 gene as depicted in FIG. 7, or an isolated or recombinant nucleic acid sequence as depicted in FIG. 7, or a vector comprising one of the above mentioned nucleic acid sequences, or a host cell capable of transferring DNA to a plant comprising said one of the above nucleotide sequences or said vector.

Such a method for providing at least partial resistance or increasing resistance in a plant against an TYLCV infection involves the transfer of DNA into a plant, i.e., involves a method for transforming a plant cell comprising providing said plant cell with a nucleic acid as described herein or a vector as described herein or a host cell as described herein.

There are multiple ways in which a recombinant nucleic acid can be transferred to a plant cell, for example *Agrobacterium* mediated transformation. However, besides by *Agrobacterium* infection, there are other means to effectively deliver of DNA to recipient plant cells when one wishes to practice the invention. Suitable methods for delivering DNA to plant cells are believed to include virtually any method by which DNA can be introduced into a cell, such as by direct delivery of DNA such as by PEG-mediated transformation of protoplasts, by desiccation/inhibition-mediated DNA uptake (Potrykus et al., Mol. Gen. Genet., 199:183-188, 1985), by electroporation (U.S. Pat. No. 5,384,253), by agitation with silicon carbide fibers (Kaeppler et al., 1990; U.S. Pat. Nos. 5,302,523; and 5,464,765), and by acceleration of DNA coated particles (U.S. Pat. Nos. 5,550,318; 5,538,877; and 5,538,880). Through the application of techniques such as these, cells from virtually any plant species may be stably transformed, and these cells developed into transgenic plants.

In case *Agrobacterium* mediated transfer is used, it is preferred to use a substantially virulent *Agrobacterium* host cell such as *A. tumefaciens*, as exemplified by strain A281 or a strain derived thereof or another virulent strain available in the art. These *Agrobacterium* strains carry a DNA region originating from the virulence region of the Ti plasmid pTiBo542 containing the virB, virC and virG genes. The virulence (vir) gene products of *A. tumefaciens* coordinate the processing of the T-DNA and its transfer into plant cells. Vir gene expression is controlled by virA and virG, whereby virA upon perception of an inducing signal activates virG by phosphorylation. VirG, in turn, induces the expression of virB, C, D, E. These genes code for proteins involved in the transfer of DNA. The enhanced virulence of pTiBo542 is thought to be caused by a hypervirulent virG gene on this Ti plasmid (Chen et al. Mol. Gen. Genet 230: 302-309, 1991).

After transfer of a nucleic acid into a plant or plant cell, it must be determined which plants or plant cells have been provided with said nucleic acid. This is for example accomplished by using a selectable marker or a reporter gene. Among the selective markers or selection genes that are most widely used in plant transformation are the bacterial neomycin phosphotransferase genes (nptI, nptII and nptIII genes) conferring resistance to the selective agent kanamycin, suggested in EP131623 and the bacterial aphIV gene suggested in EP186425 conferring resistance to hygromycin. EP 275957 discloses the use of an acetyl transferase gene from *Streptomyces viridochromogenes* that confers resistance to the herbicide phosphinotricin. Plant genes conferring relative resistance to the herbicide glyphosate are suggested in EP218571. The resistance is based on the expression of a gene encoding 5-enolshikimate-3-phosphate synthase (EPSPS) that is relatively tolerant to N-phosphomethylglycine. Certain amino acids such as lysine, threonine, or the lysine derivative amino ethyl cysteine (AEC) and tryptophan analogs like 5-methyl tryptophan can also be used as selective agents due to their ability to inhibit cell growth when applied at high concentration. In this selection system expression of the selectable marker gene results in overproduction of amino acids by transgenic cells which permits the transgenic to grow under selection. Suitable examples of reporter genes are beta-glucuronidase (GUS), beta-galactosidase, luciferase and green fluorescent protein (GFP).

Alternatively, transformants can be detected by assaying for the presence of the Ty-1 gene or the protein encoded by said gene according to methods as described above.

Another aspect of the present invention relates to a TYLCV-resistant plant, preferably a TYLCV-resistant tomato plant, that is obtained by a method according to the invention. The invention further relates to the use of a TYLCV-resistant plant according to the invention in a cross with a TYLCV-sensitive plant. It is preferred to use a TYLCV-resistant tomato plant in a cross with a tomato plant, preferably a TYLCV-sensitive tomato plant. The invention further relates to a part of a TYLCV-resistant plant, preferably a TYLCV-resistant tomato plant.

The invention also provides a plant that is obtainable by using a method for providing at least partial resistance or increasing resistance in a plant against TYLCV infection as described above. A preferred plant is a plant from the Solanaceae family and even more preferred said plant is a *Solanum lycopersicum*, formerly known as *Lycopersicon esculentum*. The invention thus also provides a plant that has been provided with a nucleic acid encoding a protein encoded by the Ty-1 gene or a functional fragment or a functional homologue thereof. Whether a plant has been provided with a nucleic acid as described herein is for example determined by using a probe or primer that has been designed based on the herein described nucleic acid sequence. One can also use methods for detection of the expression of the protein encoded by the Ty-1 gene.

The invention further provides a leaf, fruit or part or progeny of a genetically modified plant comprising a nucleic acid encoding the protein encoded by the Ty-1 gene or a functional fragment or a functional homologue thereof.

A further aspect of the invention relates to a seed, preferably a tomato seed that can be grown into a TYLCV-resistant plant according to the invention, and to methods of producing said seed. In one embodiment, the method comprises the steps of providing a TYLCV-resistant tomato plant according to the invention, crossing said TYLCV-resistant plant with a *S. lycopersicon* plant, and collecting seeds resulting from said cross, which when planted, produce TYLCV-resistant tomato plants.

In another embodiment, a method of the invention comprises the steps of providing a TYLCV-resistant tomato plant according to the invention, crossing said TYLCV-resistant plant with a *S. lycopersicon* plant, collecting seeds resulting from said cross, regenerating said seeds into plants, selecting TYLCV-resistant plants by any of the methods described herein, self-crossing the selected plants for a sufficient number of generations to obtain plants that are fixed for an allele that confers TYLCV-resistance in the plants, backcrossing the plants thus produced with *S. lycopersicon* plant plants having desirable phenotypic traits for a sufficient number of generations to obtain *S. lycopersicon* plants that are TYLCV-resistant and have desirable phenotypic traits, and collecting the seeds produced from the plants resulting from the last backcross, which when planted, produce tomato plants which are TYLCV-resistant.

It will be clear to the skilled person that the methods of producing seed that can be grown into a TYLCV-resistant plant, as detailed hereinabove for tomato, can also be used for producing seed to grow other TYLCV-resistant plant such as, for example, tobacco, pepper and potato.

By way of example, and not of limitation, Examples of the present invention will now be given.

Example

Materials and Methods

Plant Material

Two F2 populations in which Ty-1 is segregating were provided by breeding companies within the Centre for BioSystems Genomics (CBSG). Both populations were derived from commercial hybrids harboring the Ty-1 gene that is introgressed from *S. chilense* LA1969 in the genetic background of cultivated tomato *S. lycopersicium*. Plants that were selected from a recombinant screening were selfed and their F3 progenies were used for further testing with TYLCV. As susceptible control *S. lycopersicum* cv Moneymaker (MM) was included.

Markers

All markers used in this study are PCR-based CAPS markers taken from publicly available data (Table 2). Tomato BACs in the region of Ty-1 and Ty-3 were selected according to a physical map of tomato chromosome 6 {Peters, 2009; ibid} (FIG. 2) and sequences were downloaded from the SOL website. For each BAC multiple random primer pairs, which would result in products of approximately 800 bp, were designed using PrimerBLAST® from NCBI (http://www.ncbi.nlm.nih.gov/tools/primer-blast). Since the parental lines of the F.sub.2 populations could not be obtained due to confidentiality, resistant and susceptible F.sub.2 plants were selected. Two DNA-pools were made containing DNA of either 10 resistant (R) or 10 susceptible (S) F.sub.2 plants. These pools (R-pool and S-pool) were used for marker development. In case PCR products obtained from both pools showed no length polymorphism, several restriction enzymes were used to search for polymorphisms. In the same way, scaffold sequences spanning gaps between the selected BACs were used for marker development.

Recombinant Screening

Leaf samples were collected from two-week-old seedlings and DNA was extracted according to the NaOH extraction method as described {Wang et al., 1993. Nucleic Acids Research 21: 4153-4154}, with some slight modifications. In brief, small leaf samples were grinded for 5 minutes in 20 μl 0.5 M NaOH using a tissue striker (Kisan Biotech™). After addition of 20 μl of 100 mM Tris (pH 7.5), 5 μl was added to 200 μl 100 mM Tris (pH 7.5) to prepare (crude) genomic DNA template for PCR reactions.

Polymerase chain reaction (PCR) amplification was performed according to standard protocols in an Applied Biosystems GeneAmp 2700 system using the following profile: initial denaturation at 94° C. for 5 min, 35 cycles: 94° C. for 30 s, various annealing temperatures for 30 s (see Table 2), 72° C. for 1 min and final extension at 72° C. for 5 min. Amplifications were performed in 20 μl volumes containing 1 μl crude genomic DNA template, 0.1 μl Phire Hot Start DNA Polymerase (Finnzymes, Finland), 4 μl 5× Phire Reaction Buffer, 1 μl 10 μM forward primer, 1 μl 10 μM reverse primer, 1 μl 10 mM dNTP and $H_2O$ to a final volume of 20 μl. PCR products were resolved on a 1.5% agarose gel and stained with either ethidium bromide or Gelred (Biotum, California, USA).

TYLCV Inoculation Using Viruliferous Whiteflies

Two week old seedlings were put in a cage in the presence of whiteflies carrying TYLCV-Alm. After 4 days, whiteflies were killed by adding Admire (Bayer Cropscience) to the soil. After another two weeks plants were scored as R (Resistant, no symptoms) or S (Susceptible, with curling and yellowing of the leaves).

Agroinoculation

An infectious TYLCV clone (pTYCz40a, kindly provided by Dr. Eduardo Rodríguez Bejarano, Universidad de Malaga) was transformed to *Agrobacterium tumefaciens* strain LBA4404 and used to agroinoculate tomato seedlings. To this end, *A. tumefaciens* containing the TYLCV clone was grown overnight at 28° C. in 3 ml LB medium (10 $gL^{-1}$ trypton, 5 $gL^{-1}$ yeast, 4 $gL^{-1}$ NaCl, 1 $gL^{-1}$ KCl, 3 $gL^{-1}$ $MgSO_4.2H_2O$). From the overnight culture 600 μl was transferred to 3 ml induction medium (10.5 $gL^{-1}$ $K_2HPO4_4$, 4.5 $gL^{-1}$ $KH_2PO_4$, 1 $gL^{-1}$ $(NH_4)_2SO_4$, 0.5 $gL^{-1}$ Sodium citrate.$2H_2O$, 1 mM $MgSO_4.7H_2O$, 0.2% (w/v) glucose, 0.5% (v/v) glycerol; after autoclaving 50 μM acetosyringone and 10 mM MES (pH 5.6) are added) and grown overnight at 28° C. Bacteria were pelleted by centrifugation for 10 min at 5000 RCF and resuspended in MS medium (supplemented with 150 μM acetosyringone and 10 mM MES) at an $OD_{600}$ of 0.5. The first pair of true leaves of three weeks old seedlings were agroinoculated with the TYLCV construct by pressure inoculation with a syringe.

Plants were kept under greenhouse conditions at a temperature of 23° C. and relative humidity of 60% during a 16 hours day/8 hours night regime. Four weeks after agroinfiltration, plants were evaluated for TYLCV symptoms by using the disease severity index as described by {Lapidot et al., 2006. Phytopathology 96, 1404-1408}.

Fluorescence In Situ Hybridization (FISH)

Recently, FISH has been shown to facilitate genetic mapping by visualization of physical locations of BACs on pachytene chromosomes {Szinay et al., 2010. Cytogenet Genome Res 129:199-210}. Moreover, cross-species FISH has been successfully applied to detect chromosomal rearrangements between *Solanum* species {Tang et al., 2008. Genetics 180: 1319-1328; Iovene et al., 2008. Genetics 180: 1307-1317; Lou et al., 2010. Chromosoma 119: 435-442}. Therefore, BAC-FISH can be performed in introgression breeding to investigate whether chromosomal rearrangements are present between closely related species used for interspecific crosses.

Slide Preparation

Young flower buds were collected in the greenhouse and fixed overnight in fresh Carnoy solution (1:3=acetic acid: ethanol), then transferred to 70% ethanol for long term storage at +4° C. Slides were prepared according to {Szinay et al., 2008. The Plant Journal 56, 627-637} without post-fixation with 1% formaldehyde.

BAC and COT 100 Isolation and Labelling

BAC DNA was isolated using High Pure Plasmid Isolation Kit (Roche 11754785001). Isolated DNA was labeled by nick translation according to the manufacturers' protocol of Roche. Probes were labeled either directly using Cy3-dUTP (Amersham), Cy3.5-dCTP (Amersham) or indirectly with biotin or digoxigenin. Cot 100 isolation, necessary to block repeats present in most of the BACs, was performed according to {Szinay, 2008; ibid}.

FISH Procedure, Microscopy and Data Analysis

FISH experiments were performed according to {Szinay, 2008; ibid} with some slight modifications. Probes were hybridized for 48 hours at 37 C {Rens et al., 2006. Nature Protocols 1:783-790}. For the washing stringency 64% formamide {Schwarzacher and Heslop-Harrison (2000).

Practical in situ hybridization. BIOS Scientific Publishers, Oxford} was used for 3×5 minutes at 42° C. Biotin labeled probes were amplified using streptavidin-Cy5 and biotinylated anti-streptavidin. Digoxigenin labeled probes were amplified using antidig FITC and anti sheep FITC. Microscopy and data analysis were performed according to {Szinay, 2008; ibid}.

Results

Large introgression fragments are present in cultivars carrying Ty-1

In this study two $F_2$ populations, having an introgression from S. chilense LA1969 and segregating for TYLCV resistance, were used to further fine map the Ty-1 gene. Prior to the fine mapping the presence of the Ty-1 introgression was verified in both $F_2$ populations. To this end a small set of $F_2$ plants (n=45) from population-1 was challenged by viruliferous whitefly infestation. As susceptible control, MM was included in the test. Three weeks after challenging, TYLCV symptoms, i.e. yellowing and curling of the leaves, were clearly visible on MM plants (FIG. 1). From population-1, 15 $F_2$ plants showed symptoms and were scored as susceptible. In contrast, 30 $F_2$ plants remained symptomless and were scored as resistant (FIG. 1). To analyse the presence of a Ty-1 introgression in these $F_2$ plants, five markers were applied, i.e. REX-1, Aps-1, TG97, TG231 and JB-1, which previously have been reported to be linked with Ty-1 (Table 2, {Pérez de Castro, 2007; ibid}). All the tested markers showed a homozygous or heterozygous S. chilense genotype for the resistant plants and a S. lycopersicum genotype for all susceptible plants. Similar results were obtained in population-2. Thus, the presence of a Ty-1 carrying S. chilense introgression on chromosome 6 in both populations was confirmed.

The Ty-1 gene has been roughly mapped around the centromere on chromosome 6 (Zamir, 1994; ibid, Pérez de Castro, 2007; ibid). In order to fine map the Ty-1 gene and to determine the size of the Ty-1 introgression from S. chilense, additional molecular markers were generated based on the tomato genome sequence. In total, 18 BACs were selected that are physically mapped in the Ty-1 region on chromosome 6 (FIG. 2) {Peters, 2009; ibid}. For marker development, 10 resistant (R) and 10 susceptible (8) $F_2$ plants of population-1 were selected to assemble DNA-pools (see M&M) and to be subsequently analyzed for the presence of polymorphisms between R and S plants. From the 18 BACs selected, only ten were successfully converted into PCR-based CAPS markers (Table 2). For the other BACs no PCR amplification was obtained or no polymorphisms between the R- and S-pools were observed. By using a tomato scaffold sequences additional markers were successfully designed in gaps between the BAC-contigs (FIG. 2 and Table 2).

Based on polymorphisms between the R and S pools, the introgression in population-1 at least spans the region between BAC H304P16 and BAC M005H10. The introgression thus covers a part of the short arm, the centromere and a part of the long arm of chromosome 6 (FIG. 2). Markers derived from these two BACs were applied in population-2. The same marker polymorphisms were observed, suggesting that the introgression in this population is at least of the same size as that in population-1. Since both $F_2$ populations are derived from commercial $F_1$ hybrids, our results clearly demonstrate that a large chromosomal fragment from S. chilense carrying Ty-1 is introgressed into cultivated tomatoes. Based on the latest tomato sequence release (2.10) the introgression covers at least 30 million base pairs.

Suppression of Recombination in the S. Chilense Introgression Region

To further fine map Ty-1 an initial screening was performed on approximately 3000 plants from the $F_2$ population-1 with markers M304P16-2 and M005H10, which flank the chromosomal region where Ty-1 and Ty-3 are located according to previous studies {Zamir, 1994; ibid, Ji, 2007; ibid, Pérez de Castro, 2007; ibid}. This first screening yielded a total of 26 recombinants that were further genotyped with all the other markers in the region (Table 3). Those analyses surprisingly revealed that all recombination events occurred downstream of marker Msc09883-6 (FIG. 2). No recombinants were found between M304P16-2 and MSc09883-6, strongly suggesting a suppression of recombination in the region.

To test whether this suppression was population specific, another $F_2$ population ($F_2$ population-2) was used for recombinant screening. From 1600 $F_2$ plants, only 4 recombination events between M304P16-2 and M005H10 were identified. This result combined with the observations made in population 1, strongly supported the idea that recombination within this region was being suppressed.

Chromosomal Rearrangements in the S. Chilense Introgression

Suppression of recombination can be caused by high repeat content in the heterochromatin region or by chromosomal rearrangements between homologous chromosomes in introgression lines. To test for the presence of chromosomal rearrangements in the Ty-1 introgression, FISH experiments were performed. To this end, five BACs were selected, two on the short arm and three on the long arm (FIG. 3). Nine F2 plants of population-1 were used, of which three were homozygous for S. chilense alleles in the Ty-1 introgression (b plants), three homozygous for S. lycopersicum alleles (a plants) and three heterozygous (h plants). On the pachytene chromosome of the a plants, the BACs hybridized to the expected locations as in cv. MM and cv. Heinz (FIG. 3). However, on the b plants, four BACs hybridized on the long arm and only one (H176D13) on the short arm. BAC H242H19, which localized on the short arm above the centromere in a plants, showed a signal on the long arm below the centromere in b plants. Furthermore, the order of BAC H309K01 and 11003K02 was inverted between a and b plants. Whereas BAC H176D13 and 11308F14, most distal in the short and long arm pericentromere heterochromatin, were syntenic between a and b plants, it was difficult to obtain a clear signal in b plants. On the h plants one signal was observed for BAC H176D13 and H308F14. BAC H242H19 gave two signals, one on the short arm and one on the long arm. For the other two BACs, which orders were inverted between 'a' and 'b' plants, multiple signals appeared on the h plants indicating that paring between homologous chromosomes was interrupted. The results altogether suggested the occurrence of two chromosomal inversions between S. chilense LA1969 (the donor species of the Ty-1 gene) and S. lycopersicum, i.e. one involving the centromere and the other one on the long arm pericentromere heterochromatin (FIG. 3). Both inversions localized to the chromosomal region where suppression of recombination was observed (Table 3).

Finemapping of Ty-1

Using another set of Ty-1 recombinants (R1 to R13, table 6) the Ty-1 gene was fine mapped. Multiple CAPS markers in this region were developed using the same method as described before. Based on a field test the gene could be fine mapped between the markers Ty3-M3 and Ty3-M5.

In the chromosomal region flanked by M3 and M5, three recombinants are available, R7, R8 and R11 (table 6 and table 7). Selfing progeny of these three recombinants were used for a disease test with a standardized agroinoculation procedure in a climate controlled greenhouse (as described before). All progenies of recombinants R8 and R11 were susceptible (Table 8), indicating that the resistant allele of Ty-1 is not present in these two recombinant. In the progeny of R7, we had plants showing slight symptoms and plants that were fully resistant (Table 8). Genotyping these plants showed plants with slight symptoms carried homozygous *S. lycopersicum* alleles at the M5 locus. By applying more markers (Table 9), it was shown that the recombinant R7 was fixed for *S. chilense* allele in the region upstream the marker 29-30 and heterozygous in the region downstream the marker 27-28. In conclusion, the Ty-1 gene is potentially located upstream of 29-30 and downstream of Ty3-M3 (Table 7).

Interestingly, the crossing-over event in R7 occurs within the predicted gene Solyc06g51190 (FIG. 5 and FIG. 6). By sequencing parts of the gene Solyc06g51190 from all selfing progenies of R7 used in the disease test, the recombination point in R7 was pinpointed to 100 basepairs, downstream exon number 4. Plants of R7 thus have a chimeric gene Solyc06g5119. The fact that plants with the chimeric gene Solyc06g51190 showed intermediate resistance suggests that the chimeric status of the predicted gene Solyc06g51190 influenced the level of TYLCV resistance, indicating that the candidate gene Solyc06g51190 is likely (a part of) the Ty-1 gene.

Solyc06g51170, Solyc06g51180 and Solyc06g51190 are all parts of ONE RNA-Dependent RNA polymerase.

In the region of interest, between the markers Ty3-M3 and Ty3-M5 in total four putative genes are available as candidate for the genetic source of the resistance, Solyc06g51160, Solyc06g51170, Solyc06g51180 and Solyc06g51190. To analyse these genes cDNA from infected Ty-1 lines was made and the predicted genes were amplified. The obtained products were sequenced and it appeared that the three (Solyc06g51170, Solyc06g51180 and Solyc06g51190) predicted RNA-dependent-RNA polymerase were all part of one gene (FIG. 7).

Silencing of Candidate Genes

To verify the function of these predicted candidate genes present in the Ty-1 interval, Virus Induced Gene Silencing (VIGS) approach was chosen. Silencing constructs of the candidate genes Solyc06g051160, Solyc06g051180 and Solyc06g051190 were made. Silencing of two genes (Solyc06g051180 and Solyc06g051190) coding for RDRs compromised the resistance conferred by Ty-1 (FIG. 8), which forms another indication that Solyc06g51170, Solyc06g51180 and Solyc06g51190 are not three separate genes but together are only one gene. Silencing of the gene with unknown function had no effect. Altogether the results show that Ty-1 encodes an RNA-dependent RNA polymerase.

TABLE 2

CAPS markers on chromosome 6

| Name | Sequence 5'-3' | Annealing temperature | Restriction enzyme | SEQ ID NO | Reference |
|---|---|---|---|---|---|
| Aps-1 | GGCAGGAGAATATGCCAAAA CGTTCCATTCTCAACCCATT | 55° C. | TaqI | 5 6 | {Pérez de Castro, 2007} |
| REX-1 | TCGGAGCCTTGGTCTGAATT-ATGCCAGAGATGATTCGTGA | 55° C. | TaqI | 7 8 | {Pérez de Castro, 2007} |
| JB-1 | AACCATTATCCGGTTCACTC TTTCCATTCCTTGTTTCTCTG | 55° C. | TaqI | 9 10 | {Pérez de Castro, 2007} |
| TG231 | CCATCCTGATTGAAGGGAAACAAGC CTAGATGAAATGTACCATGCTGCCC | 55° C. | TaqI | 11 12 | {Ji, 2007} |
| TG97 | CACCACATAATTGAGAAGGACAACAC CATCATTGCTATTGAAGTCATCCG | 55° C. | TasI | 13 14 | {Ji, 2007} |
| M304P16-2 | AGCCCCCAGAAAGACTTGTT TTTTTAAGGGGTGTGCCAAG | 60° C. | HpyF3I | 15 16 | Present |
| M295L11-1 | GTTGGCCGGGACACCACAGT TGCTGAGGAGCTGGGAGACAA | 60° C. | aspLI | 17 18 | Present |
| M309K01-1 | ACCGGTGCATATAGAGGTCG TGAAGGGCAAGTCTCCCATA | 55° C. | TaqI | 19 20 | Present |
| M271 L05-4 | GGAAAGCAAAGAAGGCAGTG AGCCTCTACAAGCACCTCCA | 60° C. | HpyF10VI | 21 22 | Present |
| M040F08-2 | AATTACCGCTTCCTCCAGGT AATGTCTCCCCAAACAGCAC | 60° C. | HpyCH41V | 23 24 | Present |
| Msc09983-6 | GCTCCCCAACTCGCAACCTGC TGGCTCCATTCGAACCGCCA | 60° C. | BseDI | 25 26 | Present |
| Msc01216-6 | CGCTCGGCCTCGGCAAATGA CAGCCGGCGCTAAGGCATCA | 60° C. | BspLI | 27 28 | Present |
| M067G18-1 | CGACTCGTCATCTATCGCAA TTCTTGAAGGTGCTTGGCTT | 55° C. | RsaI | 29 30 | Present |

TABLE 2 -continued

CAPS markers on chromosome 6

| Name | Sequence 5'-3' | Annealing temperature | Restriction enzyme | SEQ ID NO | Reference |
|---|---|---|---|---|---|
| T1563 | ACTTCACCTACAAATCCTTCCAGA GCCCTTCCCAATCCAGCAGT | 56° C. | TaqI | 31 32 | {Ji, 2007} |
| M026P18-1 | GCATGTGTGCAGCTCACTCTCCC TCAAGTCCGAATCGAAGCCCCA | 60° C. | AluI | 33 34 | Present |
| M302A23-3 | TCCCGTCTCCTGCACCTACTTCT AAAGGGGTGGTGCTCGCCCT | 60° C. | HpyF10VI | 35 36 | Present |
| M082G10-5 | GGCATCGCCATCATCTCTAAGTCCA GCCTCAACCTACTGCCTTGCAAAT | 60° C. | FspB1 | 37 38 | Present |
| MSc05732-3 | ATGCTTTTCGAGCACGAGCCT AGCCTAAAGAGAACTAGGCAGGGGA | 55° C. | RsaI | 39 40 | Present |
| MSc05732-4 | ACGAGATGGAGCGGTCTTCAAGCT GACAGATCTCCCGGTAGGAGAGCA | 55° C. | Dde | 41 42 | Present |
| MSc05732-14 | GTGGGGCCTCGATCCCAGTCA GGCCCTTTAGTGTGTTTCACACCT | 55° C. | NcoI | 43 44 | Present |
| MSc05732-18 | TTGAGTCTGGCCTGCTCTGAATCT CATTCTGCTCGTCTTCAGAACACCTC | 55° C. | AluI | 45 46 | Present |
| C2_At3g11210 | AGGCCTGTATAGAGCTATGCAAAGAG AATTCTGTTGCCATTGATTTCCAGTG | 60° C. | HinfI | 47 48 | SGN |
| M005H10 | AAATCACCTTCCACAGTGCAG CTGGCCATAAAGTCTGGACAA | 55° C. | RsaI | 49 50 | Present |
| Ty3-M3 | AGCTCTTCCAGGAGCAGTTTG CCCTCCAAATAGTTTCACAAATACG | 58° C. | Mse I | 51 52 | Present |
| Ty3-M5 | CCGAAGGTGATAACCACGAC GCGACCCTAACCAACAATAAAC | 56° C. | BstN I | 53 54 | Present |
| Ty3-M6 | ATCAAGTATGCGCCCACGTA TTGAACGAGTTAGGCAAACAGTAAG | 56° C. | Dde I | 55 56 | Present |

TABLE 3

Selected recombinants between M304P16-2 and M005H10 identified in F2 population-1 and used in disease tests.

| Recombinant | M304P16-2 | M295L11-1 | M309K01 | M271L05-4 | M040F08-2 | MSc09883-6 | M067G18-1 | T1563 | MSc01216-6 | M026P18-1 |
|---|---|---|---|---|---|---|---|---|---|---|
| O-C11 | h | h | h | h | h | h | h | h | h | h |
| K-A5 | h | h | h | h | h | h | h | h | h | h |
| U-A2 | h | h | h | h | h | h | h | h | h | h |
| Z-G9 | b | b | b | b | b | b | b | b | b | b |
| M-G6 | h | h | h | h | h | h | h | h | h | h |
| W-G5 | a | a | a | a | a | a | a | a | a | a |
| M-a7 | b | b | b | b | b | b | b | b | b | b |
| U-f6 | b | b | b | b | b | b | b | b | b | b |
| J-D10 | a | a | a | a | a | a | a | a | a | a |
| S-F7 | b | b | b | b | b | b | b | b | b | b |
| V-A9 | h | h | h | h | h | h | h | h | h | h |
| K-D1 | b | b | b | b | b | b | b | b | b | h |
| AC-E7 | h | h | h | h | h | h | h | h | h | b |
| L-D5 | a | a | a | a | a | a | a | a | h | h |
| R-G10 | a | a | a | a | a | a | h | h | h | h |
| Z-D8 | a | a | a | a | a | a | h | h | h | h |
| R-C2 | b | b | b | b | b | b | h | h | h | h |
| T-E11 | h | h | h | h | h | h | b | b | b | b |

TABLE 3-continued

Selected recombinants between M304P16-2 and M005H10 identified in F2 population-1 and used in disease tests.

| Recom-binant | M302A23-3 | M082G10-5 | MSc05732-3 | MSc05732-4 | MSc05732-14 | MSc05732-18 | PG9 | C2 A13g11210 | M005H10 | Result of disease test on F3 progenies |
|---|---|---|---|---|---|---|---|---|---|---|
| O-C11 | h | h | h | h | h/a | h | h/b | b | b | Segregating |
| K-A5 | h | h | h | h | a/h | a | a | a | a | All susceptible |
| U-A2 | h | h | h | h | a/h | a | a | a | a | Segregating |
| Z-G9 | b | b | b | b | b | h | h/b | h | h | All resistant |
| M-G6 | h | h | h | h | b | b | b/h | b | b | Segregating |
| W-G5 | a | a | a | a | h/a | h | h/b | h | h | Segregating |
| M-a7 | b | b | b | b | h/a | h | h/b | h | h | Segregating |
| U-f6 | b | b | h | h | h/a | h | h/b | h | h | Segregating |
| J-D10 | a | h | h | h | h/a | h | h/b | h | h | Segregating |
| S-F7 | b | b | h | h | h/a | h | h/b | h | h | Segregating |
| V-A9 | a | a | a | a | a/h | a | a | a | a | All susceptible |
| K-D1 | h | h | h | h | h/a | h | h/b | h | h | Segregating |
| AC-E7 | b | b | b | b | b | b | b/h | b | b | All resistant |
| L-D5 | h | h | h | h | h/a | h | h/b | h | h | Segregating |
| R-G10 | h | h | h | h | h/a | h | h/b | h | h | Segregating |
| ZD8 | h | h | h | h | h/a | h | h/b | h | h | Segregating |
| R-C2 | h | h | h | h | h/a | h | h/b | h | h | Segregating |
| T-E11 | b | b | b | b | b | b | b/hb | b | b | All resistant | a Homozygous Solanum lycopersicum
h Heterozygous
b Homozygous Solanum chilense
nd not determined

TABLE 4

Marker genotypes of a fixed Ty-1 and a fixed Ty-3 line

| | C2_At4g01900 | 295L11-1 | C2_At5g61510 | 309K01-1 | 040F08-2 | 302A23-3 | MSc05732-4 |
|---|---|---|---|---|---|---|---|
| Ty-52 (Ty-1) | b | b+ | b | nd | b+ | b | b |
| LA 1969 | b+ | b+ | b | b | b+ | nd | b |
| Su09E941-164-1 (Ty-3) | a | a+ | a | a | a+ | a | a |
| LA 2779 | b+ | b | b | b | b+ | b | nd |

| | MSc05732-14 | PG3 | MSc05732-18 | PG9 | C2_At3g11210 | 005H10 |
|---|---|---|---|---|---|---|
| Ty-52 (Ty-1) | a | a | a | a | a+ | a |
| LA 1969 | b+ | b+ | b | b+ | b | b+ |
| Su09E941-164-1 (Ty-3) | b | b+ | b | b+ | b | b+ |
| LA 2779 | b+ | b+ | b | b | b | b+ | a Homozygous Solanum lycopersicum
b Homozygous Solanum chilense
nd not determined
+indicates this allele is specific for this line and different from the alleles in F2-population 1

TABLE 5

Plants with recombination in between MSc05732-4 and MSc05732-14.

| Recombinant | C2-At4g01900 | 304P16-2 | 295L11-1 | 309K01 | 271L05-4 | 040F08-2 | Sc09883-6 | T1563 | 067G18-1 | Sc01216-6 |
|---|---|---|---|---|---|---|---|---|---|---|
| K-A5 | h | h | h | h | h | h | h | h | h | h |
| M-G6 |   | h | h | h | h | h | h | h | h | h |
| W-G5 |   | a | a | a | a | a | a | a | a | a |
| M-A7 |   | b | b | b | b | b | b | b | b | b |

| Recombinant | 026P18-1 | 302A23-3 | T0774 | 082G10-5 | MSc05732-3 | MSc05732-4 | 17-18 | 27-28 | 31-32 | Ty3-M6 |
|---|---|---|---|---|---|---|---|---|---|---|
| K-A5 | h | h |   | h | h | h | a | a | a | a |
| M-G6 | h | h |   | h | h | h | h | h | h | b |
| W-G5 | a | a |   | a | a | a | h | h | h | h |
| M-A7 | b | b |   | b | b | b | h | h | h | h |

| Recombinant | Ty3-M8 | MSc05732-14 | MSc05732-18 | PG9 | C2_At3g11210 | 005H10 | disease test on F3 |
|---|---|---|---|---|---|---|---|
| K-A5 | a | h/a | a | a | a | a | all susceptible |
| M-G6 | b | b | b | b/h | b | b | segregating |
| W-G5 | h | a/h | h | h/b | h | h | segregating |
| M-A7 | h | a/h | h | h/b | h | h | segregating |

TABLE 6

Field disease test and genotype of recombinants

Florida recombinant inbred lines

| Line | No. of plants tested | Phenotype | Marker data | | | | | | | | |
|---|---|---|---|---|---|---|---|---|---|---|---|
|   |   |   | 304P16-2 | MSc09883-6 | T0774 | MSc05732-3 | MSc05732-4 | M1 | M3 | M4 | M5 |
| R1 | 4 | R | a | a | a | a | b | b | b | b | b |
| R2 | 3 | S | a | a | b | b | b | a | a | a | a |
| R3 | 2 | S | a | a | b | b | b | a | a | a | a |
| R4 | 4 | R | a | a | a | a | a | b | b | b | b |
| R5 | 3 | R | a | a | a | a | a | b | b | b | b |
| R6 | 6 | S | a | a | b | a | a | a | a | a | a |
| R7 | 7 | R* | a | a | b | b | b | b | b | b | a |
| R8 | 2 | S | a | a | b | b | b | b | b | a | a |
| R9 | 3 | S | a | a | b | a | a | a | a | a | a |
| R10 | 1 | S | a | a | b | b | b | a | a | a | a |
| R11 | 3 | S | a | a | a | a | a | a | a | a | b |
| R12 | 3 | R | a | a | a | a | a | b | b | b | b |
| R13 | 2 | S | a | a | b | a | a | a | a | a | a |
| R-control | 7 | R | b | b | b | b | b | b | b | b | b |
| S-control | 7 | S | a | a | a | a | a | a | a | a | b | b = *S. chilense* allele, a = *S. lycopersicum* allele
R*slight symptoms

TABLE 7

Genotypes of most informative recombinant inbred lines with additional markers

| | Inoculated/Mock | Genotype | | Disease Score 12-05 | Disease Score 19-05 | Disease Score 25-05 | | Inoculated/Mock | Genotype | Disease score 12-05 | Disease score 19-05 |
|---|---|---|---|---|---|---|---|---|---|---|---|
|   |   | MSc05732-4 | M5 |   |   |   |   |   | M6 |   |   |
| R7 #1 | Inoculated | b | a | 0.5 | 0.5 | 1 | R11 #1 | Inoculated | b | 3 | 4 |
| R7 #2 | Inoculated | b | a | 0.5 | 1 | 1 | R11 #2 | Inoculated | h | 3 | 4 |
| R7 #3 | Mock | b | b | 0 | 0 | 0 | R11 #3 | Mock | b | 0 | 0 |
| R7 #4 | Mock | b | b | 0 | 0 | 0 | R11 #4 | Mock | h | 0 | 0 |
| R7 #5 | Mock | b | h | 0 | 0 | 0 | R11 #5 | Mock | b | 0 | 0 |
| R7 #6 | Inoculated | b | a | 1 | 1 | 1 | R11 #6 | Inoculated | h | 4 | 4 |
| R7 #7 | Inoculated | b | b | 0 | 0 | 0 | R11 #7 | Inoculated | h | 4 | 4 |
| R7 #8 | Inoculated | b | h | 0 | 0 | 0 | R11 #8 | Inoculated | h | 4 | 4 |
| R7 #9 | Inoculated | b | a | 1 | 1 | 2 | R11 #9 | Inoculated | b | 4 | 4 |

TABLE 7-continued

Genotypes of most informative recombinant inbred lines with additional markers

| | | | | | | | | | | | |
|---|---|---|---|---|---|---|---|---|---|---|---|
| R7 #10 | Inoculated | b | h | 1 | 1 | 0 | R11 #10 | Inoculated | b | 4 | 4 |
| R7 #11 | Inoculated | b | h | 0 | 0 | 0 | R11 #11 | Inoculated | a | 2 | 4 |
| R7 #12 | Inoculated | b | a | 1 | 1 | 1 | R11 #12 | Inoculated | h | 2 | 4 |
| R7 #13 | Inoculated | b | h | 0 | 0 | 0 | R11 #13 | Inoculated | h | 4 | 4 |
| R7 #14 | Inoculated | b | a | 2 | 2 | 2 | | | | | |
| R7 #15 | Inoculated | b | b | 0 | 0 | 0 | | | | | |
| R7 #16 | Inoculated | b | b | 0 | 0 | 0 | | | | | |
| R7 #17 | Inoculated | b | h | 0 | 0 | 0 | | | | | |
| R7 #18 | Inoculated | b | h | 0 | 0 | 0 | | | | | |
| R7 #19 | Inoculated | b | h | 0 | 0 | 0 | | | | | |
| R7 #20 | Inoculated | b | a | 0 | 1 | 1 | | | | | |

| | Inoculated/Mock | Genotype M5c05732-4 | Disease Score 12-05 | Disease Score 19-05 | | Inoculated/Mock | Genotype M6 | Disease score 12-05 | Disease score 19-05 |
|---|---|---|---|---|---|---|---|---|---|
| R8 #1 | Inoculated | b | 4 | 4 | R12 #1 | Inoculated | b | 0 | 0 |
| R8 #2 | Inoculated | b | 4 | 4 | R12 #2 | Inoculated | h | 0 | 0 |
| R8 #3 | Mock | b | 0 | 0 | R12 #3 | Mock | b | 0 | 0 |
| R8 #4 | Mock | a | 0 | 0 | R12 #4 | Mock | h | 0 | 0 |
| R8 #5 | Mock | h | 0 | 0 | R12 #5 | Mock | b | 0 | 0 |
| R8 #6 | Inoculated | b | 4 | 4 | R12 #6 | Inoculated | b | 0 | 0 |
| R8 #7 | Inoculated | h | 4 | 4 | R12 #7 | Inoculated | a | 4 | 4 |
| R8 #8 | Inoculated | h | 4 | 4 | R12 #8 | Inoculated | a | 4 | 4 |
| R8 #9 | Inoculated | a | 4 | 4 | R12 #9 | Inoculated | b | 0 | 0 |
| R8 #10 | Inoculated | h | 4 | 4 | R12 #10 | Inoculated | a | 3 | 4 |
| R8 #11 | Inoculated | b | 4 | 4 | R12 #11 | Inoculated | h | 0 | 0 |
| R8 #12 | Inoculated | a | 4 | 4 | R12 #12 | Inoculated | h | 0 | 0 |
| R8 #13 | Inoculated | b | 4 | 4 | R12 #13 | Inoculated | b | 0 | 0 |
| R8 #14 | Inoculated | a | 4 | 4 | R12 #14 | Inoculated | b | 0 | 0 |
| R8 #15 | Inoculated | h | 4 | 4 | R12 #15 | Inoculated | h | 0 | 0 |
| R8 #16 | Inoculated | h | 0 | 0 | | | | | |
| R8 #17 | Inoculated | h | 4 | 4 | | | | | |
| R8 #18 | Inoculated | h | 2 | 4 | | | | | |
| R8 #19 | Inoculated | h | 4 | 4 | | | | | |
| R8 #20 | Inoculated | a | 4 | 4 | | | | | |
| R8 #21 | Inoculated | h | 4 | 4 | | | | | |
| R8 #22 | Inoculated | a | 4 | 4 | | | | | |
| R8 #23 | Inoculated | a | 3 | 4 | | | | | |
| R8 #24 | Inoculated | b | 4 | 4 | | | | | |
| R8 #26 | Inoculated | h | 4 | 4 | | | | | | b = *S. chilense* allele,
a = *S. lycopersicum* allele

TABLE 8

Disease test Wageningen, symptoms are scored on a scale from 0 to 4.

| | Ty3-M3 | 17-18 | Ty3-M | 25-26 | 27-28 | 29-30 | 31-32 | Ty3-M5 |
|---|---|---|---|---|---|---|---|---|
| TY-1 r7-1 | b | b | b | b | b | a | a | a |
| TY-1 r8-1 | b | a | a | a | a | a | a | a |
| TY-1 r11-1 | a | a | a | a | a | a | b | b |

(b = *S. chilense* allele, a = *S. lycopersicum* allele, h = heterozygous).
R7: two markers were used to genotype all the individuals. Plants with a *S. lycopersicum* genotype for marker M5 showed slight symptoms (disease score as 0.5 and 1).
R11 and R8: all plants are susceptible, indicating that the Ty-1 resistant allele is not presented. The resistance in plant R8#16 could be due to escape of the virus.
R12: a control line, the b and h plants are resistant and the a plants are susceptible as expected

TABLE 9

Primers used to further genotype recombinants
R7, R8 and R11 (see table 7).
Obtained products were sequenced and based
on multiple SNPs the plants could be genotyped.

| Name | Sequence | Annealing T | SEQ ID NO |
|---|---|---|---|
| 17 | CCCCCTTAGGAACATTCGTCCTCA | 55 | 57 |
| 18 | AGGGTAGGGAACAAGCCAAGGCA | | 58 |

TABLE 9 -continued

Primers used to further genotype recombinants
R7, R8 and R11 (see table 7).
Obtained products were sequenced and based
on multiple SNPs the plants could be genotyped.

| Name | Sequence | Annealing T | SEQ ID NO |
|---|---|---|---|
| 25 | TGCCAGACTCAGCATTAGTTTGGGG | 55 | 59 |
| 26 | TGTCCCCATCATGCCACACTTCCA | | 60 |
| 27 | TGTCATCTCCCAGGGCTCTCTGT | 55 | 61 |
| 28 | ACCTGTGGTGAAGGTAGTGCGGA | | 62 |
| 29 | TCTACACTATGAGCCACTGCTCGT | 55 | 63 |
| 30 | TCCTGAATCGGCCTCTGATTTGGA | | 64 |
| 31 | GCCTGGACGAATGGGAGGCAC | 55 | 65 |
| 32 | ATGGGCATCGGTCACTCGCG | | 66 |

The invention claimed is:

1. A method of producing a seed having resistance to tomato yellow leaf curl virus (TYLCV) in a plant of a *Solanaceae* family, the method comprising:
   (a) crossing genetic material comprising a region from 21.0 million base pairs (mbp) (±1 mbp) upstream the long arm of chromosome 6 to 31.8 mbp (±1 mbp) upstream the long arm of chromosome 6 from *S. chilense* into a host tomato plant to produce a progeny plant that comprises genetic material from *S. chilense*, wherein the genetic material comprises MSc05732-4 marker having SEQ ID NO:42;
   (b) backcrossing the progeny plant with the host plant to obtain a plant population;
   (c) screening for a presence of at least one Ty-1 gene in the plant population with a cleaved amplified polymorphic sequence marker (CAPS marker) that is a MSc05732-4 marker;
   (d) selecting a TYLCV-resistant plant from the plant population, wherein the TYLCV-resistant plant has expression of the at least one Ty-1 gene located between markers M067G18-1 and MSc05732-18 on chromosome 6 of the TYLCV-resistant plant; and
   (e) collecting a seed from the TYLCV-resistant plant, wherein the seed comprises the at least one Ty-1 gene and a phenotypic trait of TYLCV resistance.

2. A method of producing a tomato yellow leaf curl virus (TYLCV) resistant plant of the Solanaceae family, the method comprising:
   (a) crossing genetic material comprising a region from 21.0 million base pairs (mbp) (±1 mbp) upstream the long arm of chromosome 6 to 31.8 mbp (±1 mbp) upstream the long arm of chromosome 6 from *S. chilense* into a host plant, wherein the host plant of the Solanaceae family is a tomato plant, wherein the host plant is a tomato yellow leaf curl virus-susceptible plant, to produce a progeny plant that comprises genetic material from *S. chilense*;
   (b) backcrossing the progeny plant with the host plant to obtain a plant population;
   (c) screening for a presence of at least one Ty-1 resistant allele in the plant population with a cleaved amplified polymorphic sequence marker (CAPS marker) that is a MSc05732-4 marker;
   (d) selecting a TYLCV-resistant plant from the plant population, wherein the TYLCV-resistant plant has expression of at least one Ty-1 gene located between markers M067G18-1 and MSc05732-18 on chromosome 6 of the TYLCV-resistant plant;
   (e) collecting a seed from the TYLCV-resistant plant; and
   (f) regenerating the seed to obtain a tomato yellow leaf curl virus (TYLCV) resistant plant comprising the at least one Ty-1 gene and a phenotypic trait of TYLCV resistance.

3. The method of claim 2, further comprising genotyping the plant population as comprising homozygous Ty-1 resistant allelles or heterozygous Ty-1 resistant alleles.

4. The method of claim 2, wherein the TYLCV-susceptible plant is *S. lycopersicum*.

5. The method of claim 1, wherein the MSc05732-4 marker has a sequence comprising gacagatctc ccggtaggag agca (SEQ ID NO:42).

6. The method of claim 2, wherein the MSc05732-4 marker has a sequence comprising gacagatctc ccggtaggag agca (SEQ ID NO:42).

7. The method of claim 1, wherein the Ty-1 gene comprises CCTTCTTGTATA (SEQ ID NO:67).

8. The method of claim 2, wherein the Ty-1 gene comprises CCTTCTTGTATA (SEQ ID NO:67).

* * * * *

SEQUENCE LISTING

<160> NUMBER OF SEQ ID NOS: 68

<210> SEQ ID NO 1
<211> LENGTH: 3103
<212> TYPE: DNA
<213> ORGANISM: Solanum chilense
<220> FEATURE:
<221> NAME/KEY: CDS
<222> LOCATION: (1)..(3054)

<400> SEQUENCE: 1

| | | | | | | | | | | | | | | | | |
|---|---|---|---|---|---|---|---|---|---|---|---|---|---|---|---|---|
| atg | ggt | gat | ccg | ttg | att | gaa | gaa | att | gat | gtt | cct | tct | tgt | ata | ctg | 48 |
| Met | Gly | Asp | Pro | Leu | Ile | Glu | Glu | Ile | Asp | Val | Pro | Ser | Cys | Ile | Leu | |
| 1 | | | | 5 | | | | | 10 | | | | | 15 | | |
| gat | gca | cct | tta | cca | tat | tct | gta | gag | acg | atg | ctt | gat | aga | atc | tgc | 96 |
| Asp | Ala | Pro | Leu | Pro | Tyr | Ser | Val | Glu | Thr | Met | Leu | Asp | Arg | Ile | Cys | |
| | | | | 20 | | | | | 25 | | | | | 30 | | |
| aag | gag | cag | ggg | caa | aaa | cca | ccg | tgt | act | ggc | att | aga | agg | agg | ctg | 144 |
| Lys | Glu | Gln | Gly | Gln | Lys | Pro | Pro | Cys | Thr | Gly | Ile | Arg | Arg | Arg | Leu | |
| | | | 35 | | | | | 40 | | | | | 45 | | | |
| agc | tct | att | ggt | gaa | aaa | ggg | tca | tta | gaa | atg | ctc | aaa | ata | ata | tca | 192 |
| Ser | Ser | Ile | Gly | Glu | Lys | Gly | Ser | Leu | Glu | Met | Leu | Lys | Ile | Ile | Ser | |
| | 50 | | | | | 55 | | | | | 60 | | | | | |
| cgt | cgt | cct | atc | aag | aag | agt | ctc | tct | gct | ttt | ctt | gtt | tac | atg | att | 240 |
| Arg | Arg | Pro | Ile | Lys | Lys | Ser | Leu | Ser | Ala | Phe | Leu | Val | Tyr | Met | Ile | |
| 65 | | | | | 70 | | | | | 75 | | | | | 80 | |
| gat | cgc | tac | ccg | gat | tgt | ctc | tcc | tct | tcc | tct | agc | cca | ttc | aat | agt | 288 |
| Asp | Arg | Tyr | Pro | Asp | Cys | Leu | Ser | Ser | Ser | Ser | Ser | Pro | Phe | Asn | Ser | |
| | | | | 85 | | | | | 90 | | | | | 95 | | |
| cta | ctc | aaa | cgc | tct | tct | tcc | cct | gtt | cta | ttt | cca | tct | cca | gag | ggt | 336 |
| Leu | Leu | Lys | Arg | Ser | Ser | Ser | Pro | Val | Leu | Phe | Pro | Ser | Pro | Glu | Gly | |
| | | | 100 | | | | | 105 | | | | | 110 | | | |
| aaa | cgt | tta | caa | ggt | gaa | agt | tct | tct | aaa | tca | aag | ctt | gag | atg | ggc | 384 |
| Lys | Arg | Leu | Gln | Gly | Glu | Ser | Ser | Ser | Lys | Ser | Lys | Leu | Glu | Met | Gly | |
| | 115 | | | | | 120 | | | | | 125 | | | | | |
| tta | ttg | gcc | tgt | gca | agc | cct | cag | aaa | gtt | gct | cgc | cag | tta | tca | ttt | 432 |
| Leu | Leu | Ala | Cys | Ala | Ser | Pro | Gln | Lys | Val | Ala | Arg | Gln | Leu | Ser | Phe | |
| 130 | | | | | 135 | | | | | 140 | | | | | | |
| tgc | gag | gag | cct | gaa | tct | aac | tgt | aga | aga | acc | tcc | cct | tat | gtc | agc | 480 |
| Cys | Glu | Glu | Pro | Glu | Ser | Asn | Cys | Arg | Arg | Thr | Ser | Pro | Tyr | Val | Ser | |
| 145 | | | | | 150 | | | | | 155 | | | | | 160 | |
| caa | cag | ttg | atg | atc | ctc | aat | gaa | ctt | gaa | ttt | aga | aaa | ttg | ttt | ttg | 528 |
| Gln | Gln | Leu | Met | Ile | Leu | Asn | Glu | Leu | Glu | Phe | Arg | Lys | Leu | Phe | Leu | |
| | | | | 165 | | | | | 170 | | | | | 175 | | |
| gta | ctg | agc | tac | att | gga | tgc | aac | aag | ttg | gaa | gat | gtt | ata | tcc | cct | 576 |
| Val | Leu | Ser | Tyr | Ile | Gly | Cys | Asn | Lys | Leu | Glu | Asp | Val | Ile | Ser | Pro | |
| | | | 180 | | | | | 185 | | | | | 190 | | | |
| caa | att | gct | gat | gat | att | gta | aga | aag | aaa | gat | ctt | tcc | atg | act | gat | 624 |
| Gln | Ile | Ala | Asp | Asp | Ile | Val | Arg | Lys | Lys | Asp | Leu | Ser | Met | Thr | Asp | |
| | 195 | | | | | 200 | | | | | 205 | | | | | |
| ttt | gaa | tca | gaa | att | tgg | aat | gct | ttt | gga | aaa | gca | tgt | tat | gct | gtg | 672 |
| Phe | Glu | Ser | Glu | Ile | Trp | Asn | Ala | Phe | Gly | Lys | Ala | Cys | Tyr | Ala | Val | |
| 210 | | | | | 215 | | | | | 220 | | | | | | |
| tca | gat | aga | tca | aag | tac | tta | gac | tgg | aat | tgc | aga | aag | aca | cat | atc | 720 |
| Ser | Asp | Arg | Ser | Lys | Tyr | Leu | Asp | Trp | Asn | Cys | Arg | Lys | Thr | His | Ile | |
| 225 | | | | | 230 | | | | | 235 | | | | | 240 | |
| tac | tat | tgc | cac | att | aag | cag | aac | gga | tgc | tgt | acc | ttc | aag | ggt | cca | 768 |
| Tyr | Tyr | Cys | His | Ile | Lys | Gln | Asn | Gly | Cys | Cys | Thr | Phe | Lys | Gly | Pro | |
| | | | | 245 | | | | | 250 | | | | | 255 | | |
| tac | ttg | aac | aca | gca | agg | act | cac | tta | cag | aga | gcc | ctg | gga | gat | gac | 816 |
| Tyr | Leu | Asn | Thr | Ala | Arg | Thr | His | Leu | Gln | Arg | Ala | Leu | Gly | Asp | Asp | |

```
            260                 265                 270
aat gta ctg att gtc aaa ttt gtt gaa gat aca agt tgt gcc aat ata    864
Asn Val Leu Ile Val Lys Phe Val Glu Asp Thr Ser Cys Ala Asn Ile
        275                 280                 285 att ctc gag gaa ggc att ctt gtt ggc ttg aga cgt tac cgt ttc ttt    912
Ile Leu Glu Glu Gly Ile Leu Val Gly Leu Arg Arg Tyr Arg Phe Phe
290                 295                 300 gtg tat aaa gat gat aaa gag agg aag aaa agt cca gct atg atg aag    960
Val Tyr Lys Asp Asp Lys Glu Arg Lys Lys Ser Pro Ala Met Met Lys
305                 310                 315                 320 aca aaa act gct tct ttg aag tgc tac ttt gtt agg ttt gag tcc att   1008
Thr Lys Thr Ala Ser Leu Lys Cys Tyr Phe Val Arg Phe Glu Ser Ile
            325                 330                 335 gga acc tgc gat gat gga gaa tcc tat gta ttt tct acc aaa aca atc   1056
Gly Thr Cys Asp Asp Gly Glu Ser Tyr Val Phe Ser Thr Lys Thr Ile
            340                 345                 350 agt caa gca agg tgt aaa ttc atg cat gtg cat atg gtt tct aat atg   1104
Ser Gln Ala Arg Cys Lys Phe Met His Val His Met Val Ser Asn Met
            355                 360                 365 gca aaa tat gca gcc agg ctt tcc tta att cta tca aag act att aag   1152
Ala Lys Tyr Ala Ala Arg Leu Ser Leu Ile Leu Ser Lys Thr Ile Lys
370                 375                 380 ctt caa gtg gat ctt gat tct gtc acc att gaa aga atc gaa gat ata   1200
Leu Gln Val Asp Leu Asp Ser Val Thr Ile Glu Arg Ile Glu Asp Ile
385                 390                 395                 400 ctt tgt cgg gat gaa aat ggt tgt att att caa gat gaa gac ggc gaa   1248
Leu Cys Arg Asp Glu Asn Gly Cys Ile Ile Gln Asp Glu Asp Gly Glu
                405                 410                 415 cct cgt ata cat act gat ggt act ggt ttc ata tca gaa gat tta gct   1296
Pro Arg Ile His Thr Asp Gly Thr Gly Phe Ile Ser Glu Asp Leu Ala
            420                 425                 430 atg cat tgt ccc aaa gat ttt tca aaa gca gaa tat ata aaa gat gaa   1344
Met His Cys Pro Lys Asp Phe Ser Lys Ala Glu Tyr Ile Lys Asp Glu
            435                 440                 445 aat tat gag aat ttt gtt gat atc gtg gac ctt gat gac gtg aat gta   1392
Asn Tyr Glu Asn Phe Val Asp Ile Val Asp Leu Asp Asp Val Asn Val
450                 455                 460 gaa aga aga gcg agt gta tct ggg aat agg gaa ccg cct ttg ttg atg   1440
Glu Arg Arg Ala Ser Val Ser Gly Asn Arg Glu Pro Pro Leu Leu Met
465                 470                 475                 480 cag tgc cgt ttg ttc ttc aac ggt tgt gct gtg aag ggg act ttt ctt   1488
Gln Cys Arg Leu Phe Phe Asn Gly Cys Ala Val Lys Gly Thr Phe Leu
                485                 490                 495 gtc aat aga aag att gga tca cga aaa att cat att aga ccc tca atg   1536
Val Asn Arg Lys Ile Gly Ser Arg Lys Ile His Ile Arg Pro Ser Met
            500                 505                 510 gtg aag gtt gag ata gac cca aca att tca agt ata cca act ttt gac   1584
Val Lys Val Glu Ile Asp Pro Thr Ile Ser Ser Ile Pro Thr Phe Asp
            515                 520                 525 tca ttg gag ata gtt gca atc agt cat aga cca aat aag gca tat ctg   1632
Ser Leu Glu Ile Val Ala Ile Ser His Arg Pro Asn Lys Ala Tyr Leu
530                 535                 540 tcc aag aat tta atc tct ctg ctg agc tac gga gga gtc cat aaa gaa   1680
Ser Lys Asn Leu Ile Ser Leu Leu Ser Tyr Gly Gly Val His Lys Glu
545                 550                 555                 560 tac ttt ctg gag ctt ttg gga agt gca ctg gaa gag acg aaa caa gta   1728
Tyr Phe Leu Glu Leu Leu Gly Ser Ala Leu Glu Glu Thr Lys Gln Val
                565                 570                 575 tat ttg agg aaa cgg gca gct cta aaa gtt gct atc aac tat aga gaa   1776
```

```
Tyr Leu Arg Lys Arg Ala Ala Leu Lys Val Ala Ile Asn Tyr Arg Glu
            580                 585                 590 atg gat gat gaa tgt cta aca gca agg atg ata tcg tct ggg ata cct      1824
Met Asp Asp Glu Cys Leu Thr Ala Arg Met Ile Ser Ser Gly Ile Pro
            595                 600                 605 ctc aat gaa cct cat ctc cat gtt cgc ttg tct agg ctt gca aag att      1872
Leu Asn Glu Pro His Leu His Val Arg Leu Ser Arg Leu Ala Lys Ile
            610                 615                 620 gaa aga act aag ctt aga gga gga aag ctt cct ata agt gac agt ttt      1920
Glu Arg Thr Lys Leu Arg Gly Gly Lys Leu Pro Ile Ser Asp Ser Phe
625                 630                 635                 640 tat ctt atg gga aca gct gac ccc act ggt gta ctg gaa agc aat gaa      1968
Tyr Leu Met Gly Thr Ala Asp Pro Thr Gly Val Leu Glu Ser Asn Glu
                645                 650                 655 gtc tgt gct att cta gat aat ggc caa gta tct ggg cgt gtt ttg gtc      2016
Val Cys Ala Ile Leu Asp Asn Gly Gln Val Ser Gly Arg Val Leu Val
                660                 665                 670 tac aga aat cct ggt ctt cac ttt gga gat gtg cat gtg atg aaa gcg      2064
Tyr Arg Asn Pro Gly Leu His Phe Gly Asp Val His Val Met Lys Ala
            675                 680                 685 cga tat gtg gaa gag ctt gca gat gtt gtt ggt gat gcc aaa tat ggt      2112
Arg Tyr Val Glu Glu Leu Ala Asp Val Val Gly Asp Ala Lys Tyr Gly
            690                 695                 700 ata ttt ttt tca act aaa ggc ccg agg tca gct gct act gag att gca      2160
Ile Phe Phe Ser Thr Lys Gly Pro Arg Ser Ala Ala Thr Glu Ile Ala
705                 710                 715                 720 aat ggt gac ttt gat ggt gat atg tat tgg gtt tcc ata aac cgt aag      2208
Asn Gly Asp Phe Asp Gly Asp Met Tyr Trp Val Ser Ile Asn Arg Lys
                725                 730                 735 ttg gta gat tct tat aca aca agt aga cca tgg att cgc atg cat tca      2256
Leu Val Asp Ser Tyr Thr Thr Ser Arg Pro Trp Ile Arg Met His Ser
                740                 745                 750 act cct aag gca gtt agc aaa aaa cca agt gaa ttt tca gct gat gaa      2304
Thr Pro Lys Ala Val Ser Lys Lys Pro Ser Glu Phe Ser Ala Asp Glu
            755                 760                 765 ttg gaa tat gag ctt ttc agg caa ttt ctg gaa gca aag tct aaa ggt      2352
Leu Glu Tyr Glu Leu Phe Arg Gln Phe Leu Glu Ala Lys Ser Lys Gly
770                 775                 780 gcc aat atg tct ctg gca gct gat agc tgg ctg gca ttt atg gat cgt      2400
Ala Asn Met Ser Leu Ala Ala Asp Ser Trp Leu Ala Phe Met Asp Arg
785                 790                 795                 800 ctt ctg atg ctg cga gat gat aat gtg gat gat atg cat agc ttg aaa      2448
Leu Leu Met Leu Arg Asp Asp Asn Val Asp Asp Met His Ser Leu Lys
                805                 810                 815 ggc aag atg ctt cac ctg att gac atc tac tat gat gca tta gat gca      2496
Gly Lys Met Leu His Leu Ile Asp Ile Tyr Tyr Asp Ala Leu Asp Ala
            820                 825                 830 cct aaa agc ggg aag aag gtt agc atc cct cat tat ctg aag gca aac      2544
Pro Lys Ser Gly Lys Lys Val Ser Ile Pro His Tyr Leu Lys Ala Asn
            835                 840                 845 aag ttc ccc cac tat atg gaa aaa ggg aac tcc tgc agc tat cat tca      2592
Lys Phe Pro His Tyr Met Glu Lys Gly Asn Ser Cys Ser Tyr His Ser
            850                 855                 860 act tct att ctg ggt cag att tat gat cat gtc gac tca tat cca gat      2640
Thr Ser Ile Leu Gly Gln Ile Tyr Asp His Val Asp Ser Tyr Pro Asp
865                 870                 875                 880 gaa gat ttg tgt ata aca gag atc tct aaa ctg cct tgc ttt gaa gtt      2688
Glu Asp Leu Cys Ile Thr Glu Ile Ser Lys Leu Pro Cys Phe Glu Val
                885                 890                 895
```

-continued

| | | |
|---|---|---|
| gaa atc cct caa aga tgc atg aca ttg tgg aga gga aga tat gaa gag<br>Glu Ile Pro Gln Arg Cys Met Thr Leu Trp Arg Gly Arg Tyr Glu Glu<br>900                         905                        910 | 2736 | |
| tac aaa aag gat atg aca cag gcc atg aac tta gat tgt gaa ctt aga<br>Tyr Lys Lys Asp Met Thr Gln Ala Met Asn Leu Asp Cys Glu Leu Arg<br>915                         920                        925 | 2784 | |
| atc acc tct tgc aat gaa gtt ata aag aag tac aag atg ttg cta tat<br>Ile Thr Ser Cys Asn Glu Val Ile Lys Lys Tyr Lys Met Leu Leu Tyr<br>930                         935                        940 | 2832 | |
| ggt gct gtg gag ttt gaa caa aca gta aga aag act gaa gac att ttc<br>Gly Ala Val Glu Phe Glu Gln Thr Val Arg Lys Thr Glu Asp Ile Phe<br>945                         950                        955                        960 | 2880 | |
| gat gaa gcc ctt gca ata tat cat gta aca tat gat aat gca agg atc<br>Asp Glu Ala Leu Ala Ile Tyr His Val Thr Tyr Asp Asn Ala Arg Ile<br>965                         970                        975 | 2928 | |
| aca tac agc ata gag aaa tgt ggt ttt gct tgg aaa gta gct ggt tct<br>Thr Tyr Ser Ile Glu Lys Cys Gly Phe Ala Trp Lys Val Ala Gly Ser<br>980                         985                        990 | 2976 | |
| gcg ctt tgc agg atc cac gcc atg tat cgc aag gaa aaa gac ttg ccc<br>Ala Leu Cys Arg Ile His Ala Met Tyr Arg Lys Glu Lys Asp Leu Pro<br>995                         1000                      1005 | 3024 | |
| att ttg cca tcg gtt ttg cag gaa ata ctc tagtgtattg taacattgaa<br>Ile Leu Pro Ser Val Leu Gln Glu Ile Leu<br>    1010                        1015 | 3074 | |
| gtgatcaata aatatctact tagtattct | 3103 | |

```
<210> SEQ ID NO 2
<211> LENGTH: 1018
<212> TYPE: PRT
<213> ORGANISM: Solanum chilense

<400> SEQUENCE: 2

Met Gly Asp Pro Leu Ile Glu Glu Ile Asp Val Pro Ser Cys Ile Leu
1               5                   10                  15

Asp Ala Pro Leu Pro Tyr Ser Val Glu Thr Met Leu Asp Arg Ile Cys
            20                  25                  30

Lys Glu Gln Gly Gln Lys Pro Pro Cys Thr Gly Ile Arg Arg Arg Leu
        35                  40                  45

Ser Ser Ile Gly Glu Lys Gly Ser Leu Glu Met Leu Lys Ile Ile Ser
    50                  55                  60

Arg Arg Pro Ile Lys Lys Ser Leu Ser Ala Phe Leu Val Tyr Met Ile
65                  70                  75                  80

Asp Arg Tyr Pro Asp Cys Leu Ser Ser Ser Ser Pro Phe Asn Ser
                85                  90                  95

Leu Leu Lys Arg Ser Ser Pro Val Leu Phe Pro Ser Pro Glu Gly
            100                 105                 110

Lys Arg Leu Gln Gly Glu Ser Ser Lys Ser Lys Leu Glu Met Gly
        115                 120                 125

Leu Leu Ala Cys Ala Ser Pro Gln Lys Val Ala Arg Gln Leu Ser Phe
    130                 135                 140

Cys Glu Glu Pro Glu Ser Asn Cys Arg Arg Thr Ser Pro Tyr Val Ser
145                 150                 155                 160

Gln Gln Leu Met Ile Leu Asn Glu Leu Glu Phe Arg Lys Leu Phe Leu
                165                 170                 175

Val Leu Ser Tyr Ile Gly Cys Asn Lys Leu Glu Asp Val Ile Ser Pro
            180                 185                 190

Gln Ile Ala Asp Asp Ile Val Arg Lys Lys Asp Leu Ser Met Thr Asp
```

-continued

```
            195                 200                 205
Phe Glu Ser Glu Ile Trp Asn Ala Phe Gly Lys Ala Cys Tyr Ala Val
    210                 215                 220

Ser Asp Arg Ser Lys Tyr Leu Asp Trp Asn Cys Arg Lys Thr His Ile
225                 230                 235                 240

Tyr Tyr Cys His Ile Lys Gln Asn Gly Cys Cys Thr Phe Lys Gly Pro
                245                 250                 255

Tyr Leu Asn Thr Ala Arg Thr His Leu Gln Arg Ala Leu Gly Asp Asp
            260                 265                 270

Asn Val Leu Ile Val Lys Phe Val Glu Asp Thr Ser Cys Ala Asn Ile
        275                 280                 285

Ile Leu Glu Glu Gly Ile Leu Val Gly Leu Arg Arg Tyr Arg Phe Phe
    290                 295                 300

Val Tyr Lys Asp Asp Lys Glu Arg Lys Ser Pro Ala Met Met Lys
305                 310                 315                 320

Thr Lys Thr Ala Ser Leu Lys Cys Tyr Phe Val Arg Phe Glu Ser Ile
                325                 330                 335

Gly Thr Cys Asp Asp Gly Glu Ser Tyr Val Phe Ser Thr Lys Thr Ile
            340                 345                 350

Ser Gln Ala Arg Cys Lys Phe Met His Val His Met Val Ser Asn Met
        355                 360                 365

Ala Lys Tyr Ala Ala Arg Leu Ser Leu Ile Leu Ser Lys Thr Ile Lys
    370                 375                 380

Leu Gln Val Asp Leu Asp Ser Val Thr Ile Glu Arg Ile Glu Asp Ile
385                 390                 395                 400

Leu Cys Arg Asp Glu Asn Gly Cys Ile Ile Gln Asp Glu Asp Gly Glu
                405                 410                 415

Pro Arg Ile His Thr Asp Gly Thr Gly Phe Ile Ser Glu Asp Leu Ala
            420                 425                 430

Met His Cys Pro Lys Asp Phe Ser Lys Ala Glu Tyr Ile Lys Asp Glu
        435                 440                 445

Asn Tyr Glu Asn Phe Val Asp Ile Val Asp Leu Asp Asp Val Asn Val
    450                 455                 460

Glu Arg Arg Ala Ser Val Ser Gly Asn Arg Glu Pro Pro Leu Leu Met
465                 470                 475                 480

Gln Cys Arg Leu Phe Phe Asn Gly Cys Ala Val Lys Gly Thr Phe Leu
                485                 490                 495

Val Asn Arg Lys Ile Gly Ser Arg Lys Ile His Ile Arg Pro Ser Met
            500                 505                 510

Val Lys Val Glu Ile Asp Pro Thr Ile Ser Ser Ile Pro Thr Phe Asp
        515                 520                 525

Ser Leu Glu Ile Val Ala Ile Ser His Arg Pro Asn Lys Ala Tyr Leu
    530                 535                 540

Ser Lys Asn Leu Ile Ser Leu Leu Ser Tyr Gly Gly Val His Lys Glu
545                 550                 555                 560

Tyr Phe Leu Glu Leu Leu Gly Ser Ala Leu Glu Glu Thr Lys Gln Val
                565                 570                 575

Tyr Leu Arg Lys Arg Ala Ala Leu Lys Val Ala Ile Asn Tyr Arg Glu
            580                 585                 590

Met Asp Asp Glu Cys Leu Thr Ala Arg Met Ile Ser Ser Gly Ile Pro
        595                 600                 605

Leu Asn Glu Pro His Leu His Val Arg Leu Ser Arg Leu Ala Lys Ile
    610                 615                 620
```

Glu Arg Thr Lys Leu Arg Gly Gly Lys Leu Pro Ile Ser Asp Ser Phe
625                 630                 635                 640

Tyr Leu Met Gly Thr Ala Asp Pro Thr Gly Val Leu Glu Ser Asn Glu
            645                 650                 655

Val Cys Ala Ile Leu Asp Asn Gly Gln Val Ser Gly Arg Val Leu Val
            660                 665                 670

Tyr Arg Asn Pro Gly Leu His Phe Gly Asp Val His Val Met Lys Ala
            675                 680                 685

Arg Tyr Val Glu Glu Leu Ala Asp Val Val Gly Asp Ala Lys Tyr Gly
            690                 695                 700

Ile Phe Phe Ser Thr Lys Gly Pro Arg Ser Ala Ala Thr Glu Ile Ala
705                 710                 715                 720

Asn Gly Asp Phe Asp Gly Asp Met Tyr Trp Val Ser Ile Asn Arg Lys
                725                 730                 735

Leu Val Asp Ser Tyr Thr Thr Ser Arg Pro Trp Ile Arg Met His Ser
            740                 745                 750

Thr Pro Lys Ala Val Ser Lys Lys Pro Ser Glu Phe Ser Ala Asp Glu
            755                 760                 765

Leu Glu Tyr Glu Leu Phe Arg Gln Phe Leu Glu Ala Lys Ser Lys Gly
            770                 775                 780

Ala Asn Met Ser Leu Ala Ala Asp Ser Trp Leu Ala Phe Met Asp Arg
785                 790                 795                 800

Leu Leu Met Leu Arg Asp Asp Asn Val Asp Asp Met His Ser Leu Lys
                805                 810                 815

Gly Lys Met Leu His Leu Ile Asp Ile Tyr Tyr Asp Ala Leu Asp Ala
            820                 825                 830

Pro Lys Ser Gly Lys Lys Val Ser Ile Pro His Tyr Leu Lys Ala Asn
            835                 840                 845

Lys Phe Pro His Tyr Met Glu Lys Gly Asn Ser Cys Ser Tyr His Ser
850                 855                 860

Thr Ser Ile Leu Gly Gln Ile Tyr Asp His Val Asp Ser Tyr Pro Asp
865                 870                 875                 880

Glu Asp Leu Cys Ile Thr Glu Ile Ser Lys Leu Pro Cys Phe Glu Val
                885                 890                 895

Glu Ile Pro Gln Arg Cys Met Thr Leu Trp Arg Gly Arg Tyr Glu Glu
                900                 905                 910

Tyr Lys Lys Asp Met Thr Gln Ala Met Asn Leu Asp Cys Glu Leu Arg
            915                 920                 925

Ile Thr Ser Cys Asn Glu Val Ile Lys Lys Tyr Lys Met Leu Leu Tyr
            930                 935                 940

Gly Ala Val Glu Phe Glu Gln Thr Val Arg Lys Thr Glu Asp Ile Phe
945                 950                 955                 960

Asp Glu Ala Leu Ala Ile Tyr His Val Thr Tyr Asp Asn Ala Arg Ile
                965                 970                 975

Thr Tyr Ser Ile Glu Lys Cys Gly Phe Ala Trp Lys Val Ala Gly Ser
            980                 985                 990

Ala Leu Cys Arg Ile His Ala Met Tyr Arg Lys Glu Lys Asp Leu Pro
            995                 1000                1005

Ile Leu Pro Ser Val Leu Gln Glu Ile Leu
        1010                1015

<210> SEQ ID NO 3
<211> LENGTH: 3091

```
<212> TYPE: DNA
<213> ORGANISM: Solanum lycopersicum
<220> FEATURE:
<221> NAME/KEY: CDS
<222> LOCATION: (1)..(33)

<400> SEQUENCE: 3 atg ggt gat ccg ttg att gaa gaa att gat gtt ctggatgcac ctttaccata    53
Met Gly Asp Pro Leu Ile Glu Glu Ile Asp Val
1               5                  10 ttctgtagag acgatgcttg atagaatctg caaggagcag gggcaaaaac caccgtgtac    113
tggcattaga aggaggctga gctctattgg tgaaaaaggg tcattagaaa tgctcaaaat    173
aatatcacgt cgtcctatca agaagagtct ctctgctttt cttgtttaca tgattgatcg    233
ctacccggat tgtctctcct cttcctctag ccccttcaat tgtctactca aacgctcttc    293
ttcccctcgt ctctttccat ctccagaggg taaacgttta caaggtgaaa gttcttctaa    353
atcaaagctt gagatgggct tattggcctg tgcaagccct cagaaagttg ctcgccagtt    413
atcattttgc gaggagcctg aatctaactg tagaagaacc tcccttatg tcagccaaca    473
gttgatgatc ctcaatgaac ttgaatttag aaaattgttt ctggtactga gctacattgg    533
atgcaacaag ttggaagatg ttatatcccc tcaaattgct gatgatattg taagaaagaa    593
aaatctttcc atgactgatt tgaatcaga atttggaat gcttttggaa agcatgttta    653
tgctgtgtca gatagatcaa agtacttaga ctggaattgc agaaagacac atatctacta    713
ttgccacatt aagcagaacg atactgttc cttcaagggt ccatacttga acacattaag    773
gactcactta cagagagccc tgggagatga caatgtactg attgtaaaat tgttgaaga    833
tacaagttgt gccaatataa ttctcgagga aggcattctt gttggcttga acgttaccg    893
tttctttgtg tataaagatg ataaagagag aagaaaagt ccagctatga tgaagacaaa    953
aactgcttct ttgaagtgct actttgttag gtttgagtcc attggaacct gcaatgatgg    1013
agaatcctat gtattttcta ccaaaacaat cagtcaagca aggtgtaaat tcatgcatgt    1073
gcatatggtt tctaatatgg caaaatatgc agccaggctt tccttaattc tatcaaagac    1133
gattaagctt caaacagatc ttgattctgt caccattgaa agaattgaag atatactttg    1193
tcgggatgaa atggttgta ttattcaaga tgaagacggc gaacctcgta tacatactga    1253
tggtactggt tcatatcag aagatttagc tatgcattgt cccaaagatt ttcaaaagc    1313
agaatatata aaagatgaaa attatgagaa ttttgttgat atcgtggacc ttgatgacgt    1373
gaatgtagaa agaagagtga gtgtatctcg caataggaaa ccgcctttgt tgatgcagtg    1433
ccgtttgttc ttcaatggtt gtgctgtgaa ggggactttt cttgtcaata gaaagattgg    1493
atcacgaaaa attcatatta gaccctcaat ggtgaaggtt gagatagacc caacaatttc    1553
aagtatacca acttttgact cattggagat agttgcaatc agtcatagac caaataaggc    1613
atatctgtcc aagaatttaa tctctctgct gagctacgga ggagtccata agaatactt    1673
tatggaactt ttgggaagtg cgctggaaga gacgaaacaa gtatattga ggaaacgtgc    1733
agctctaaaa gttgctatca actatagaga aatggatgat gaatgtctaa cagcaaggat    1793
gatatcgtct gggataccct tcaatgaacc tcatctccat gctcgcttgt ctaggcttgc    1853
aaagattgaa agaactaagc ttagaggagg aaagcttcct ataagtgaca gtttttatct    1913
tatgggaaca gctgacccca ctggtgtact ggaaagcaat gaagtctgtg ttattctaga    1973
taatggccaa gtatctgggc gtgttttggt ctatagaaat cctggtcttc actttggaga    2033
tgtacatgtg atgaaagcgc gatatgtgga agagcttgca gatgttgttg gtgatgccaa    2093
```

```
atatggtata ttttttttcaa ctaaaggccc gaggtcagct gctactgaga ttgcaaatgg    2153
tgactttgat ggtgatatgt attgggtttc cataaaccgt aagttggtag attcttatac    2213
aacaagtaga ccatggattc gcatgcattc aactcctaac gcagttagca aaaaaccaag    2273
tgaattttca gctgatgaat tggaatatga gcttttttagg caatttctgg aagcaaagtc    2333
taaaggtgcc aatatgtctc tggcagctga tagctggctg gcatttatgg atcgtcttct    2393
gacgctgcga gatgataatg tggatgtatat gcatagcttg aaaggcaaga tgcttcacct    2453
gattgacatc tactatgatg cattagatgc acctaaaagc gggaagaagg ttagcatccc    2513
tcattatctg aaggcaaaca agttcccccca ctatatggaa aaagggaact cctgcagcta    2573
tcattcaact tctattctgg gtcagattta tgatcatgtc gactcatatc cagatgaaga    2633
tttgtgtata acagaaatct ctaaactgcc ttgctttgaa gttgaaatcc ctcaaagatg    2693
catgacattg tggagaggaa gatatgaaga gtacaaaaag gatatgacac gggccatgaa    2753
ctttgattgt gaactaagaa tcacctcttg caatgaagtt ataaagaagt acaagatgtt    2813
gctatatggt gctgtggagt ttgaacaaac agtaagaaag actgaagaca ttttcgacga    2873
ggcccttgca atatatcatg taacatatga taatgcaagg atcacataca gcatagagaa    2933
atgtggtttt gcttggaaag tagctggttc tgcgctttgc aggatccacg ccatgtatcg    2993
caaggaaaaa gacttgccca ttttgccatc ggttttgcag gaaatactct agcgtattgt    3053
aacattgaag tgatcaataa atatctactt agcattct                            3091

<210> SEQ ID NO 4
<211> LENGTH: 11
<212> TYPE: PRT
<213> ORGANISM: Solanum lycopersicum

<400> SEQUENCE: 4

Met Gly Asp Pro Leu Ile Glu Glu Ile Asp Val
1               5                   10

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      CAPS Aps-1 oligonucleotide

<400> SEQUENCE: 5
ggcaggagaa tatgccaaaa                                                  20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      CAPS Aps-1 oligonucleotide

<400> SEQUENCE: 6
cgttccattc tcaacccatt                                                  20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
```

CAPS REX-1 oligonucleotide

<400> SEQUENCE: 7
tcggagcctt ggtctgaatt                                                    20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      CAPS REX-1 oligonucleotide

<400> SEQUENCE: 8
atgccagaga tgattcgtga                                                    20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      CAPS JB-1 oligonucleotide

<400> SEQUENCE: 9
aaccattatc cggttcactc                                                    20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      VAPS JB-1 oligonucleotide

<400> SEQUENCE: 10
tttccattcc ttgtttctct g                                                  21

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      CAPS TG231 oligonucleotide

<400> SEQUENCE: 11
ccatcctgat tgaagggaaa caagc                                              25

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      CAPS TG23 oligonucleotide

<400> SEQUENCE: 12
ctagatgaaa tgtaccatgc tgccc                                              25

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      CAPS TG97 oligonucleotide

<400> SEQUENCE: 13
caccacataa ttgagaagga caacac        26

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      CAPS TG97 oligonucleotide

<400> SEQUENCE: 14
catcattgct attgaagtca tccg        24

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      CAPS M304P16-2 oligonucleotide

<400> SEQUENCE: 15
agcccccaga aagacttgtt        20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      CAPS M304P16-2 oligonucleotide

<400> SEQUENCE: 16
tttttaaggg gtgtgccaag        20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      CAPS M295L11-1 oligonucleotide

<400> SEQUENCE: 17
gttggccggg acaccacagt        20

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      CAPS M295L11-1 oligonucleotide

<400> SEQUENCE: 18
tgctgaggag ctgggagaca a        21

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      CAPS M309K01-1 oligonucleotide

<400> SEQUENCE: 19
accggtgcat atagaggtcg                                               20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      CAPS M309K01-1 oligonucleotide

<400> SEQUENCE: 20
tgaagggcaa gtctcccata                                               20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      CAPS M271L05-4 oligonucleotide

<400> SEQUENCE: 21
ggaaagcaaa gaaggcagtg                                               20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      CAPS M271L05-4 oligonucleotide

<400> SEQUENCE: 22
agcctctaca agcacctcca                                               20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      CAPS M040F08-2 oligonucleotide

<400> SEQUENCE: 23
aattaccgct tcctccaggt                                               20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      CAPS M040F08-2 oligonucleotide

<400> SEQUENCE: 24
aatgtctccc caaacagcac                                               20

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      CAPS Msc09983-6 oligonucleotide

<400> SEQUENCE: 25
gctccccaac tcgcaacctg c        21

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      CAPS Msc09983-6 oligonucleotide

<400> SEQUENCE: 26
tggctccatt cgaaccgcca        20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      CAPS Msc01216-6 oligonucleotide

<400> SEQUENCE: 27
cgctcggcct cggcaaatga        20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      CAPS Msc01216-6 oligonucleotide

<400> SEQUENCE: 28
cagccggcgc taaggcatca        20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      CAPS M067G18-1 oligonucleotide

<400> SEQUENCE: 29
cgactcgtca tctatcgcaa        20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      CAPS M067G18-1 oligonucleotide

<400> SEQUENCE: 30
ttcttgaagg tgcttggctt        20

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      CAPS T1563 oligonucleotide

<400> SEQUENCE: 31

```
acttcaccta caaatccttc caga                                          24
```

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      CAPS T1563 oligonucleotide

<400> SEQUENCE: 32

```
gcccttccca atccagcagt                                               20
```

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      CAPS M026P18-1 oligonucleotide

<400> SEQUENCE: 33

```
gcatgtgtgc agctcactct ccc                                           23
```

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      CAPS M026P18-1 oligonucleotide

<400> SEQUENCE: 34

```
tcaagtccga atcgaagccc ca                                            22
```

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      CAPS M302A23-3 oligonucleotide

<400> SEQUENCE: 35

```
tcccgtctcc tgcacctact tct                                           23
```

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      CAPS M302A23-3 oligonucleotide

<400> SEQUENCE: 36

```
aaagggtgg tgctcgccct                                                20
```

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic
      CAPS M082G10-5 oligonucleotide

<400> SEQUENCE: 37

```
ggcatcgcca tcatctctaa gtcca                                         25
```

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      CAPS M082G10-5 oligonucleotide

<400> SEQUENCE: 38
gcctcaacct actgccttgc aaat                                          24

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      CAPS MSc05732-3 oligonucleotide

<400> SEQUENCE: 39
atgcttttcg agcacgagcc t                                             21

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      CAPS MSc05732-3 oligonucleotide

<400> SEQUENCE: 40
agcctaaaga gaactaggca gggga                                         25

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      CAPS MSc05732-4 oligonucleotide

<400> SEQUENCE: 41
acgagatgga gcggtcttca agct                                          24

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      CAPS MSc05732-4 oligonucleotide

<400> SEQUENCE: 42
gacagatctc ccggtaggag agca                                          24

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      CAPS MSc05732-14 oligonucleotide

<400> SEQUENCE: 43
gtggggcctc gatcccagtc a                                             21

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      CAPS MSc05732-14 oligonucleotide

<400> SEQUENCE: 44 ggcccttag tgtgtttcac acct                                              24

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      CAPS MSc05732-18 oligonucleotide

<400> SEQUENCE: 45
ttgagtctgg cctgctctga atct                                             24

<210> SEQ ID NO 46
<211> LENGTH: 26
<212> TYPE: DNA
<213> ORGANISM: Artificial Sequence
<220> FEATURE:
<223> OTHER INFORMATION: Description of Artificial Sequence: Synthetic
      CAPS MSc05732-18 oligonucleotide

<400> SEQUENCE: 46
cattctgctc gtcttcagaa cacctc                                           26

<210> SEQ ID NO 47
<211> LENGTH: 26
<212> TYPE: DNA
<213> ORGANISM: Artificial Sequence
<220> FEATURE:
<223> OTHER INFORMATION: Description of Artificial Sequence: Synthetic
      CAPS C2_At3g11210 oligonucleotide

<400> SEQUENCE: 47
aggcctgtat agagctatgc aaagag                                           26

<210> SEQ ID NO 48
<211> LENGTH: 26
<212> TYPE: DNA
<213> ORGANISM: Artificial Sequence
<220> FEATURE:
<223> OTHER INFORMATION: Description of Artificial Sequence: Synthetic
      CAPS C2_At3g11210 oligonucleotide

<400> SEQUENCE: 48
aattctgttg ccattgattt ccagtg                                           26

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      CAPS M005H10 oligonucleotide

<400> SEQUENCE: 49
aaatcacctt ccacagtgca g                                                21

```
<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      CAPS M005H10 oligonucleotide

<400> SEQUENCE: 50
ctggccataa agtctggaca a                                              21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      CAPS Ty3-M3 oligonucleotide

<400> SEQUENCE: 51
agctcttcca ggagcagttt g                                              21

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence: Synthetic
      CAPS Ty3-M3 oligonucleotide

<400> SEQUENCE: 52
ccctccaaat agtttcacaa atacg                                          25

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      CAPS Ty3-M5 oligonucleotide

<400> SEQUENCE: 53
ccgaaggtga taaccacgac                                                20

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: Synthetic
      CAPS Ty3-M5 oligonucleotide

<400> SEQUENCE: 54
gcgaccctaa ccaacaataa ac                                             22

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      CAPS Ty3-M6 oligonucleotide

<400> SEQUENCE: 55
atcaagtatg cgcccacgta                                                20

<210> SEQ ID NO 56
```

```
<211> LENGTH: 25
<212> TYPE: DNA
<213> ORGANISM: Artificial Sequence
<220> FEATURE:
<223> OTHER INFORMATION: Description of Artificial Sequence: Synthetic
      CAPS Ty3-M6 oligonucleotide

<400> SEQUENCE: 56
ttgaacgagt taggcaaaca gtaag                                        25

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cccccttagg aacattcgtc ctca                                         24

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
agggtaggga acaagccaag gca                                          23

<210> SEQ ID NO 59
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tgccagactc agcattagtt tgggg                                        25

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tgtccccatc atgccacact tcca                                         24

<210> SEQ ID NO 61
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
tgtcatctcc cagggctctc tgt                                          23

<210> SEQ ID NO 62
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
acctgtggtg aaggtagtgc gga                                           23

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
tctacactat gagccactgc tcgt                                          24

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
tcctgaatcg gcctctgatt tgga                                          24

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gcctggacga atgggaggca c                                             21

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
atgggcatcg gtcactcgcg                                               20

<210> SEQ ID NO 67
<211> LENGTH: 12
<212> TYPE: DNA
<213> ORGANISM: Artificial Sequence
<220> FEATURE:
<223> OTHER INFORMATION: Description of Artificial Sequence: Synthetic
      indel Ty-1 gene oligonucleotide

<400> SEQUENCE: 67
ccttcttgta ta                                                       12

<210> SEQ ID NO 68
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 68

Asp Phe Asp Gly Asp
1               5
```